United States Patent
Sultan et al.

(10) Patent No.: US 12,293,001 B2
(45) Date of Patent: May 6, 2025

(54) REFERENTIAL DATA GROUPING AND TOKENIZATION FOR LONGITUDINAL USE OF DE-IDENTIFIED DATA

(71) Applicant: LexisNexis Risk Solutions FL Inc., Boca Raton, FL (US)

(72) Inventors: Jay Sultan, Bogart, GA (US); Jeffrey M. Diamond, Milton, GA (US); Jill Luber, Atlanta, GA (US); Victor E. Tavernini, Davie, FL (US); Emily Mortimer, Bloomington, MN (US); Raghunandan Valluri, Cumming, GA (US); Theresa Roseanne Wu, Winter Garden, FL (US); Charles Edwards Morton, Austin, TX (US); Brian Richard Mullin, Budd Lake, NJ (US)

(73) Assignee: LexisNexis Risk Solutions FL In., Boca Raton, FL (US)

( * ) Notice: Subject to any disclaimer, the term of this patent is extended or adjusted under 35 U.S.C. 154(b) by 288 days.

(21) Appl. No.: 17/724,908

(22) Filed: Apr. 20, 2022

(65) Prior Publication Data
US 2022/0343021 A1 Oct. 27, 2022

Related U.S. Application Data

(60) Provisional application No. 63/179,014, filed on Apr. 23, 2021.

(51) Int. Cl.
*G06F 21/62* (2013.01)
*G16H 10/60* (2018.01)
*G16H 70/40* (2018.01)

(52) U.S. Cl.
CPC ......... *G06F 21/6254* (2013.01); *G16H 10/60* (2018.01); *G16H 70/40* (2018.01)

(58) Field of Classification Search
CPC ... G06Q 50/20–26; G16H 10/60; G16H 70/40
See application file for complete search history.

(56) References Cited

U.S. PATENT DOCUMENTS

| 8,275,850 B2 * | 9/2012 | Kohan ................... G16H 10/60 709/212 |
| 9,323,892 B1 * | 4/2016 | Paris, III ............... H04L 63/102 |

(Continued)

FOREIGN PATENT DOCUMENTS

| EP | 3096258 A1 * | 11/2016 | ........... G06F 16/285 |

OTHER PUBLICATIONS

D. Jiang, A. K. H. Tung and G. Chen, "MAP-Join-Reduce: Toward Scalable and Efficient Data Analysis on Large Clusters," in IEEE Transactions on Knowledge and Data Engineering, vol. 23, No. 9, pp. 1299-1311, Sep. 2011, doi: 10.1109/TKDE.2010.248. (Year: 2011).*

(Continued)

*Primary Examiner* — Christopher L Gilligan
*Assistant Examiner* — Jessica Marie Webb
(74) *Attorney, Agent, or Firm* — TROUTMAN PEPPER LOCKE LLP; James E. Schulz; Mark Lehi Jones

(57) ABSTRACT

Systems and methods are disclosed for the utilization of personally identifiable information (PII) to identify an individual while de-identifying the associated data through tokenization. A method includes receiving, at a main tokenizer and from a first trading partner, a first data set comprising a first subset of a plurality of PII fields corresponding to an individual, receiving, at the main tokenizer and from a second trading partner, a second data set comprising a second subset of the plurality of PII fields corresponding to the individual, resolving, a the main tokenizer, the individual, linking a unique patient-centric token (PCT) to the (Continued)

individual based on the resolving, and outputting the PCT for generating a non-PII token linked to the individual.

26 Claims, 10 Drawing Sheets

(56) References Cited

U.S. PATENT DOCUMENTS

| | | | | |
|---|---|---|---|---|
| 10,255,419 | B1* | 4/2019 | Kragh | H04L 9/321 |
| 2002/0073138 | A1* | 6/2002 | Gilbert | G16Z 99/00 |
| | | | | 709/201 |
| 2002/0165853 | A1 | 11/2002 | Gogolak | |
| 2008/0147554 | A1* | 6/2008 | Stevens | G16H 10/60 |
| | | | | 705/51 |
| 2009/0094059 | A1* | 4/2009 | Coleman | G16C 20/30 |
| | | | | 705/2 |
| 2010/0241595 | A1* | 9/2010 | Felsher | G16H 10/65 |
| | | | | 707/E17.014 |
| 2015/0161413 | A1* | 6/2015 | Calem | G06F 21/6245 |
| | | | | 705/51 |
| 2016/0063191 | A1* | 3/2016 | Vesto | G16H 50/50 |
| | | | | 705/2 |
| 2016/0071208 | A1* | 3/2016 | Straub | G06Q 40/03 |
| | | | | 705/38 |
| 2016/0086262 | A1* | 3/2016 | Straub | G06Q 50/265 |
| | | | | 705/38 |
| 2016/0189293 | A1* | 6/2016 | Christiansen | G06Q 40/03 |
| | | | | 705/38 |
| 2016/0321406 | A1* | 11/2016 | Timmerman | G06Q 10/10 |
| 2018/0307859 | A1* | 10/2018 | LaFever | H04L 63/20 |
| 2019/0236310 | A1 | 8/2019 | Austin et al. | |
| 2020/0082922 | A1* | 3/2020 | Bacastow | G16H 10/60 |
| 2020/0294635 | A1* | 9/2020 | Blum | G16H 10/60 |

OTHER PUBLICATIONS

Kulshrestha et al. "Take charge of your data: How tokenization makes data usable without sacrificing privacy." Google Cloud. Jun. 26, 2019 (Jun. 26, 2019) Retrieved on Jul. 4, 2022 (Jul. 4, 2022) from <https://cloud.google.com/blog/products/identity-security/take-charge-of-your-data-how-tokenization-makes-data-usable-without-sacrificing-privacy> entire document.

Lexisnexis Risk Solutions Group. "The Health Care Business of LexisNexis Risk Solutions Improves the Precision of Deidentified Data Exchange Across Healthcare with the LexisNexis® Patient Centric Token." Nov. 9, 2021 (09.11.2021) Retrieved on Jul. 4, 2022 (Jul. 4, 2022) from <https://risk.lexisnexis.com/about-us/press-room/press-release/20211109-patient-centric-token> entire document.

* cited by examiner

| Fname | Lname | Address | Zip | DoB | Token |
|---|---|---|---|---|---|
| Jane | Smith | 123 Main | 11111 | 1/1/2000 | A |
| Janet | Smith | 123 Main | 11111 | 1/1/2000 | A |
| Jane | Smith | 123 Oak | 22222 | 1/1/2000 | B |
| Jane | Jones | 123 Oak | 22222 | 1/2/2000 | C |
| Jane | Smith | 345 Main | 11111 | 7/1/2000 | D |

FIG. 1A

| Fname | Lname | Address | Zip | DoB | Token |
|---|---|---|---|---|---|
| Jane | Smith | 123 Main | 11111 | 1/1/2000 | A |
| Janet | Smith | 123 Main | 11111 | 1/1/2000 | A |
| Jane | Smith | 123 Oak | 22222 | 1/1/2000 | A |
| Jane | Jones | 123 Oak | 22222 | 1/2/2000 | A |
| Jane | Smith | 345 Main | 11111 | 7/1/2000 | C |

FIG. 1B

| Fname | Lname | Address | Zip | DoB | PCT |
|---|---|---|---|---|---|
| Jane | Smith | 123 Main | 11111 | 1/1/2000 | 101 |
| Janet | Smith | 123 Main | 11111 | 1/1/2000 | 102 |
| Jane | Smith | 123 Oak | 22222 | 1/1/2000 | 101 |
| Jane | Jones | 123 Oak | 22222 | 1/2/2000 | 101 |
| Jane | Smith | 345 Main | 11111 | 7/1/2000 | 103 |

FIG. 1C

Trading Partner 1

| Fname | Lname | Address | Zip | DoB |
|---|---|---|---|---|
| Jane | Smith | 123 Main | 11111 | |

Trading Partner 2

| Fname | Lname | Address | Zip | DoB |
|---|---|---|---|---|
| Jane | Smith | | | 1/1/2000 |

FIG. 1D

REFERENTIAL DATA GROUPING AND TOKENIZATION FOR LONGITUDINAL USE OF DE-IDENTIFIED DATA

CROSS-REFERENCE TO RELATED APPLICATIONS

This application claims priority to U.S. Provisional Patent Application No. 63/179,014, filed 23 Apr. 2021, the contents of which are incorporated herein by reference as if presented in full.

FIELD

The disclosed technology generally relates to healthcare privacy, and in particular, to the utilization of de-identified or tokenized personally identifiable information (PII) to protect patient privacy.

BACKGROUND

Healthcare professionals utilize electronic medical records (EMR) and certain protected health information (PHI) to provide appropriate care for identified patients and to assess their treatments. PHI can include demographic information, medical histories, lab results, mental health evaluations, insurance information, and other data that can be used to identify an individual. Much of this data is highly protected by numerous regulations and other privacy rules, most notably the Health Insurance Portability and Accountability Act (HIPAA). Researches and policy makers often need to utilize clinical data (that can include PHI and/or EMR) for clinical trials, pandemic response studies, drug interaction studies, utilization reviews, establishment of guidelines, etc. However, such data is often siloed, isolated, and/or subject to privacy regulations that can collectively inhibit valuable clinical information that could be derived by sharing patient-specific information with other researchers or healthcare businesses.

HIPAA and the Health Information Technology for Economic and Clinical Health (HITECH) Act of 2009 regulate collected PHI data so that it is protected and not shared with anyone (except for certain exceptions). Such regulations also limit what organizations can do with the data in terms of marketing. Thus, the widespread use of healthcare data to drive insights and build a safer healthcare system has been severely limited due to the lack of solutions that enable sharing of data without running afoul of privacy rules.

For over 20 years, healthcare businesses have relied on basic tokenization as a means to work with de-identified data in a manner that protects patient privacy. Clinical and research scientists use anonymized PHI to study health and healthcare trends. Researchers can use PHI that is stripped of identifying features and added anonymously to large databases of patient information for population health management efforts. The identifying parts of the data are typically removed and replaced with a "token" which is often a hash (one-way cryptographic function) of the PH values. Multiple fields can be hashed together to reduce reidentification risk. If different data sets from different sources are hashed identically, then the dataset can be linked by the common token value.

There are numerous limitations in the current technology that are driven by the limits of data and tokenization or matching methodology being used. Imagine two entities (trading partners) that want to exchange (trade) healthcare data, for example, to understand trends, costs, therapy outcomes, etc. Each trading partner has data to identify the patient in their associated records, but that data has two important limitations: (1) the identifying data elements/fields and methods used by each trading partner may be different; and (2) the values of data elements/fields possessed by each trading partner may not match for the same person.

Current methods use common data attributes/elements/fields, such as first name, last name, address, zip code, date of birth, gender, etc., to create the tokens used to match data. The use of a social security number (SSN) could be used as an identifier, but SSN information is not always readily available, it can be prone to error (mis-keyed data) and it is often discouraged/prohibited by government regulation. Each trading partner might have different identity data available (i.e., trading partner A has last name and zip code, and trading partner B has last name and date of birth). To enable the broadest ability to combine data between such trading partners, it is necessary to create multiple tokens of different permutations of the identity data. Thus, an individual may have multiple tokens associated with their identity:

Token 1: first name+last name+address.
Token 2: last name+address+zip code
Token 3: last name+zip code
Token 4: last name+zip code+date of birth
and so on, for numerous other permutations, hoping for a combination that is available and matches with the data possessed by the other trading partner.

Furthermore, in addition to the different field values used, there are different methodologies used to translate (or hash) the values to a token. The same method (often the same software) must be used by both trading partners.

In a person's life, the data used to identify them often changes many times. People change their name, through marriage or through use (John S. Doe becomes J. Steven Doe). People move to multiple addresses and multiple zip codes during their life. Current methods can use probabilistic matching to try to address such differences (Jon Doe may be the same as Jonathan Doe), but these methods have severe limits, especially with difficult cases, such as a father and son with the same name at the same address, or twins with similar names). Because it is dangerous to "assume too much" when doing probabilistic matching, the current methods create different token values, for example, John Doe at zip code 12345 and Jonathan Doe at zip code 12345 may have separate associated tokens although they may be the same person in reality. Once created this way, data for Jon Doe across these two addresses cannot be combined since they appear to be two separate people.

The need to create numerous tokens using multiple methods is a problem that causes inefficiencies and inaccuracies in data matching because it is impractical to create a token for every possible permutation and method. Working with many different permutations leads to reduced coverage in any given combination of data sets, as a given data set may not have values for all the rows. For example, a dataset may have names for all records but addresses for only some. If an address is being used to link to another data set (because it is the only data field in common), then a smaller number of rows will be combined between the two data sets, greatly reducing their value and utility. Another problem that greatly reduces the value of the data exchange occurs when the data is not completely longitudinal.

The goal of tokenization is to create associations of all records for a single person in the resulting data set. However, this goal is thwarted because current processes separate data about a single person across multiple tokens (due to changes or differences in a person's identity data) that cannot be combined in the resulting data set.

A need exists for a token that is patient-centric, that does not depend upon both trading partners having the same identity fields, can solve for differences or changes in a single person's identity vales (such as name or address), and that can enable sharing of data without running afoul of privacy regulations. A need exists for patient-centric token systems and methods that can more efficiently harvest data from medical records, clinical trials, pandemic responses, etc. while protecting personally identifiable information.

BRIEF SUMMARY

The disclosed technology utilizes tokenization as a method of replacing Personally Identifiable information (PII) and/or identifying Protected Health Information (PHI) and/or non-specific industry information with non-sensitive placeholder tokens. Certain implementations of the disclosed technology may de-identify (or anonymize) such data so that cannot be re-identified (tied back to a specific, identifiable individual) and so that it is no longer subject to HIPAA or many other privacy restrictions. Certain implementations of the disclosed technology may then can be linked to other de-identified data with a common token. Thus, tokenization allows entities to link data assets together or link external data assets with internal data assets without violating privacy rules.

Certain exemplary implementations of the disclosed technology may utilize patient-centric tokenization and referential data to more quickly and efficiently harvest valuable information associated with clinical trials and/or post-trial evaluations. Certain exemplary implementations of the disclosed technology may utilize patient-centric tokenization and referential data to more effectively harvest valuable information associated with pandemic responses. Certain exemplary implementations of the disclosed technology may utilize pharmacy data for the prevention of adverse drug interactions. Certain exemplary implementations may use such data to detect and/or prevent prescription fraud. Certain implementations of the disclosed technology may be suitable for health care applications involving Protected Health information (PHI). Certain implementations of the disclosed technology may be utilized for non-industry-specific applications to protect Personally Identifiable information (PII).

In accordance with certain exemplary implementations of the disclosed technology, a computer-implemented method is provided for the creation of a dataset that can be used for detecting and preventing potential adverse reactions of prescription drug combinations. The method can include receiving, at a main tokenizer, and from at a trusted $3^{rd}$ party in communication with one or more pharmacies, one or more corresponding data sets comprising: a subset of a plurality of PII fields corresponding to a patient seeking a prescription drug; and an identifier corresponding to the prescription drug. The method includes resolving, by the main tokenizer in communication with a universal reference database, an identity of the patient based on the subset of the plurality of PII fields, linking a unique patient-centric token (PCT) to the patient based on the resolving, and determining, based on the one or more data sets, one or more prescription drug combinations associated with the resolved identity of the patient. For each of the one or more prescription drug combinations, the method includes comparing the identifiers against safety data, and determining, based on the comparing, a potential adverse reaction associated with the one or more prescription drug combinations. The method includes outputting the PCT and an indication of the potential adverse reaction.

A computer-implemented method is provided for detecting and preventing prescription drug fraud. The method includes receiving, at a main tokenizer, and from at a trusted $3^{rd}$ party in communication with one or more pharmacies, one or more corresponding data sets that can include a subset of a plurality of PII fields corresponding to a patient seeking a prescription drug prescribed by a physician, an identifier corresponding to the prescription drug, and an identifier corresponding to the physician. The method can include resolving, by the main tokenizer in communication with a universal reference database, an identity of the patient based on the subset of the plurality of PII fields, linking a unique patient-centric token (PCT) to the patient based on the resolving, determining, based on the one or more data sets, one or more over-prescription conditions of the prescription drug associated with the resolved identity of the patient, and outputting the PCT and an indication of the over-prescription condition.

Another computer-implemented method is provided. The method includes receiving, at a main tokenizer and from a first trading partner, a first data set comprising a first subset of a plurality of PII fields corresponding to an individual, receiving, at the main tokenizer and from a second trading partner, a second data set comprising a second subset of the plurality of PII fields corresponding to the individual, resolving, at the main tokenizer, the individual based on the first subset of the plurality of PII fields and the second subset of the plurality of PII fields, linking a unique patient-centric token (PCT) to the individual based on the resolving, and outputting the PCT for generating a non-PII token linked to the individual, wherein the non-PII token is linked to the universal identifier corresponding to the individual.

In accordance with certain exemplary implementations of the disclosed technology, a computer-implemented method is provided for the creation of a dataset that can be used for evaluating post-clinical trials. The method can include receiving, at a main tokenizer, and from at a trusted $3^{rd}$ party, one or more corresponding data sets comprising: a subset of a plurality of PII fields corresponding to a patient in a clinical trial, post-clinical trial health record information, and an identifier corresponding to a treatment. The method includes resolving, by the main tokenizer in communication with a universal reference database, an identity of the patient based on the subset of the plurality of PII fields, linking a unique patient-centric token (PCT) to the patient based on the resolving, and determining, based on the one or more data sets, one or more outcomes associated with the resolved identity of the patient. For each of the one or more outcomes, the method includes determining the efficacy of the clinical trial. The method includes outputting the PCT and an indication of the efficacy.

In accordance with certain exemplary implementations of the disclosed technology, a computer-implemented method is provided for the creation of a dataset that can be used for evaluating response to a public health issue, such as a pandemic. The method can include receiving, at a main tokenizer, and from a trusted $3^{rd}$ party, one or more corresponding data sets comprising: a subset of a plurality of PII fields corresponding to a patient who has received treatment, and an identifier corresponding to a treatment. The method includes resolving, by the main tokenizer in communication with a universal reference database, an identity of the patient based on the subset of the plurality of PII fields, linking a unique patient-centric token (PCT) to the patient based on the resolving, and determining, based on the one or more data sets, one or more treatment outcomes associated with the resolved identity of the patient. The method includes outputting the PCT and an indication of the one or more treatment outcomes.

Other implementations, features, and aspects of the disclosed technology are described in detail herein and are considered a part of the claimed disclosed technology. Other implementations, features, and aspects can be understood with reference to the following detailed description, accompanying drawings, and claims.

BRIEF DESCRIPTION OF THE DRAWINGS

Reference will now be made to the accompanying figures and flow diagrams, which are not necessarily drawn to scale, and wherein:

FIG. 1A depicts an example tokenization result using traditional predictive matching methods.

FIG. 1B depicts another example tokenization result using another predictive matching method that generates different token assignments compared to the example tokenization process of FIG. 1A even though the PII data is the same.

FIG. 1C depicts an example tokenization result using an improved tokenization process that utilizes unique identifiers for linking and clustering identity information in accordance with certain exemplary implementations of the disclosed technology.

FIG. 1D in illustrates a scenario where a first trading partner and a second trading partner have different information for an individual, and therefore, cannot reliably trade information using traditional methods.

DETAILED DESCRIPTION

Figure 2:
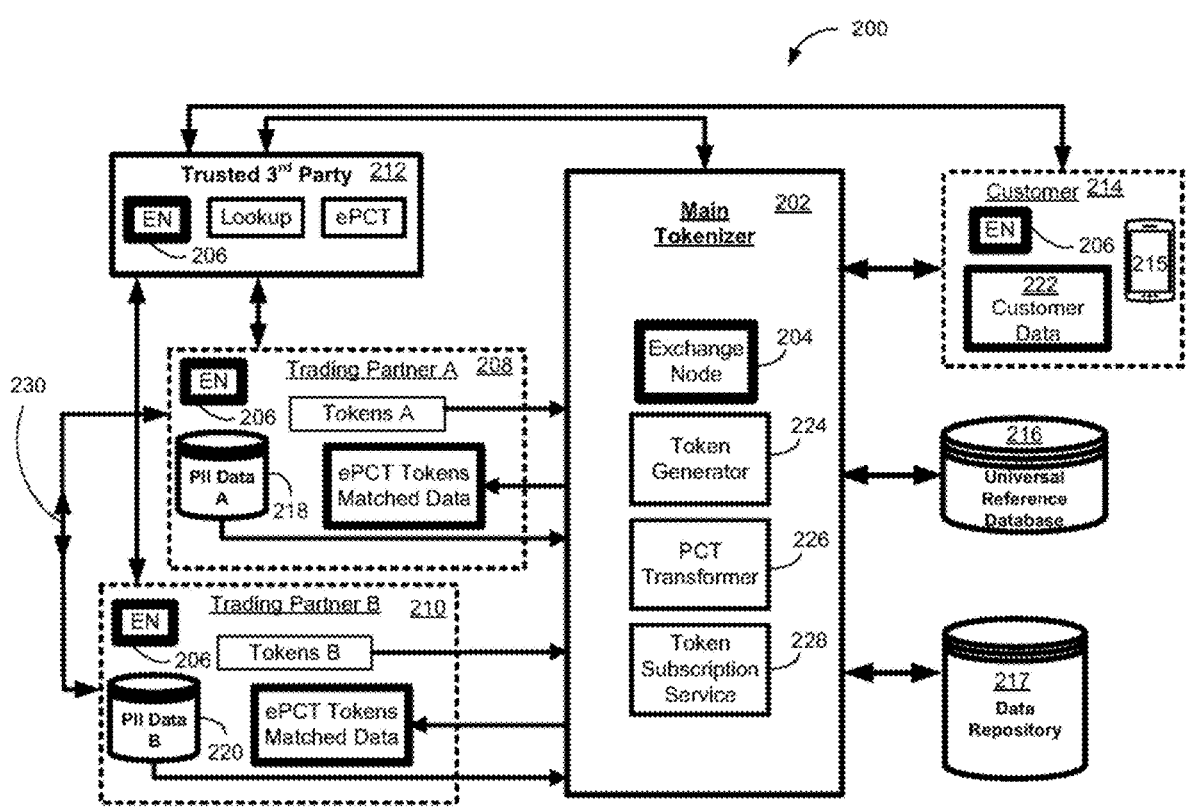
FIG. 2 illustrates an example tokenization system 200 (and associated process) that can resolve a universal identifier of an individual and use tokens to de-identify matched data to enable data trading without exposing the individual's personally identifiable information (PII), in accordance with certain exemplary implementations of the disclosed technology.

Various example embodiments of the disclosed technology now will be described more fully hereinafter with reference to the accompanying drawings, in which some, but not all embodiments of the disclosure are shown. This technology may, however, be embodied in many different forms and should not be construed as limited to the implementations set forth herein; rather, these implementations are provided so that this disclosure will be thorough and complete, and will convey the scope of the disclosed technology to those skilled in the art.

The disclosed technology can utilize referential data (a third data set) in such a way that a patient-centric token (PCT) can be created, which may be a single token that can aggregate different permutations of possibly incomplete or mismatched Personally Identifiable Information (PII) data. Certain exemplary implementations of the disclosed, technology may enable trading partners to exchange certain types of healthcare (or other) data associated with individuals without exposing the identity of such individuals.

The term patient-centric token, (or PCT), as defined herein, may refer to the identity of a specific person by a non-sensitive data element. The process of generating a PCT leverages a reference data set to resolve patient or person identity between two data sets, allowing HIPAA-de-identified data transfers that aggregate data around a single actual person.

The terms PCT and ePCT, as defined herein, are tokens that can be used to reference the identity of a specific person. According to an example implementation, the PCT and/or the ePCT may be expressed by a non-sensitive data element that is undecipherable (i.e., not traceable back to the original PII) by any person or organization. In another implementation, a mechanism or process may be provided to allow a Trusted $3^{rd}$ Party to decipher the PCT and/or the ePCT. In yet another example implementation, a mechanism or process may be provided that prevents deciphering of the PCT and or ePCT so that, for example, it is not possible for any $3^{rd}$ Party (trusted or not), trading partner, main tokenizer, and/or customer to use the PCT or ePCT to determine the original PII. In accordance with certain exemplary implementations of the disclosed technology, the mechanism or process to allow or prevent deciphering the PCT or ePCT may include one or more flags that may be set. A first flag, for example, may be set to indicate that the creator of the PCT or ePCT can or cannot translate the PCT or ePCT to a different token. A second flag, for example, may be set to indicate that anyone can or cannot translate the PCT or ePCT to a different token. In this respect, the flags may provide a way to control whether a token can be translated or deciphered by a customer, $3^{rd}$ party, trading partner, main tokenizer, and/or any other party. In certain implementations, a service may be provided to only the PCT or ePCT originator (or token generator) that allows setting of the flags. Further illustrations of how such flags may be used will be discussed below in the use-case examples. In certain exemplary implementations, the ePCT may have an additional layer of security so it may be customer or data partner-specific. The ePCTs provide stable, repeatable ways of creating a token for a person's identity that is specific to that target organization. In certain implementations, ePCTs may be accessed and/or used with possession of a digital key, for example, that can be specific to an organization such that no other organization will have access to these digital key values.

Certain exemplary implementations of the disclosed technology may utilize referential data to reduce multiple references to the same individual to produce a single de-identified token, which may be in the form of a PCT or ePCT, depending on the destination or possessing party.

One benefit and technological improvement enabled by the disclosed technology is that it does not require that trading partners use the same tokenization or matching methodology or data fields for exchanging certain data with other trading partners. The disclosed technology may combine data longitudinally for a single person despite changes or variations in their identity data. In health-care applications, for example, a Patient-Centric Token (PCT) may be generated to link all available information about a patient, overcoming variations in the patient's Personally Identifiable Information (PII), thus providing a longitudinally continuous and comprehensive view of a patient.

In accordance with certain exemplary implementations, the PCT may utilize a unique, non-SSN-dependent universal identifier. For example, certain key identifying attributes/elements/fields (name, address, date of birth, gender, etc.,) may be used in the tokenization process. Certain implementations may utilize a data asset, such as a Universal Reference Database (URD), that has comprehensive knowledge of substantially all people whose data might be traded. In accordance with certain exemplary implementations of the disclosed technology, the URD may enable performing longitudinal tokenization even if incomplete attributes/elements/fields or different permutations or variations of such attributes/elements/fields are received.

Certain implementations of the disclosed technology may utilize the URD to match against the PII of each trading partner and then group by universal identifier to make the resulting client-specific ePCT tokens patient-centric.

Certain implementations of the disclosed technology may further anonymize the PCT, for example, to produce an electronic patient-centric token (ePCT) to further reduce or eliminate the possibility of linking such data back to an individual. In accordance with certain exemplary implementations of the disclosed technology, a trusted $3^{rd}$ party may be utilized to "wall-off" or "insulate" trading partners and the main tokenizer.

As may be appreciated by those having skill in the art, the disclosed technology addresses a long-felt need to solve real-world practical problems associated with harvesting healthcare-related data while maintaining patient privacy. While the disclosed technology may be applied to solve many other problems, the following example use case descriptions illustrate certain technical problems that the disclosed technology can solve to address real-life problems.

Example Use Case 1: Clinical Trials and Post-Trial Analysis

Clinical trials typically involve human participants who receive specific interventions according to the research plan or protocol created by the investigators. These interventions may include medical products, such as drugs or devices; procedures; or changes to participants' behavior, such as diet. Clinical trials may compare a new medical approach to a standard one that is already available, to a placebo that contains no active ingredients, or to no intervention. When a new product or approach is being studied, it is not usually known whether it will be helpful, harmful, or no different than available alternatives (including no intervention). Investigators try to determine the safety and efficacy of the intervention by measuring certain outcomes in the participants.

Potential and/or enrolled participants provide consent to participate in a clinical trial based on information provided by the researchers. This information helps people decide whether they want to enroll or continue to participate in the study. The informed consent process is intended to protect participants and should provide enough information for a person to understand the risks, potential benefits, and alternatives to the study. In general, participants sign an informed consent document before joining a study to confirm that he or she was given information on the risks, potential benefits, and alternatives and that he or she understands it. However, signing the document and providing consent is not a contract, as participants may withdraw from a study at any time, even if the study is not over. In general, a patient who agrees to participate in a clinical trial may also provide consent for their doctor and/or hosptital(s) to share their associated patient data with the (pharma) company that is conducting the study. Such consent to share data typically ends when the study ends, which can prevent gathering valuable long-term follow-up data. Scenarios can exist where certain hospital patients have a condition making them suitable (or even ideal) subjects for participating in a pharmaceutical company's clinical trial or post-trial study. The hospital may be considered an aggregator in the sense that they can gather patient health and treatment histories and PII, but due to privicay laws, the hospital can't share the PII with the pharmaceutical company. As discussed above, the disclosed technology may enable a service that can be called only by the aggregator (hospital in this example) to set certain flags that control the PCT or ePCT translation permission to different tokens. Which may allow the hospital to share de-dentified patient health and treatment histories (associated with a token) with the pharmaceutical company, who can review such information without knowing the patient identity. If the de-identified patient health/treatment history is suitable for the study, the pharmaceutical company (who does not know the patient identity) could request that the hospital contact the patient who is associated with the de-identified token to let the patient know about the study. In this respect, the coordination and communication with potential trial subjects may proceed without running afoul of privacy laws.

The development, patenting, marketing, and subsequent patent expiration of the acid reflux drugs Priolsec® and Nexium® may be used to illustrate additional use case examples where post-trial harvesting of data using the disclosed technology could help reduce drug prices. AstraZeneca's patent on Prilosec® was set to expire in 2001, allowing generic manufacturers to produce their own versions, thus driving the price down. AstraZeneca's solution was to revise an isomer in the Priolosec® formulation, patent the revised formulation, and heavily market it as Nexium®. This isomer revision is a common strategy in drug development, and it can sometimes yield a better drug if one isomer turns out to produce substantially better results than the other. However, Medicare and certain health-insurance companies refused to pay for the higher-priced Nexium® without sufficient proof of added benefits to warrant the high cost of Nexium® over the generic version. Even though AstraZeneca's marketing campaign was successful in establishing Nexitum® as the go-to prescription for gastroesophageal reflux disease, AstraZeneca's commissioned follow-on studies of Nexium®'s effectiveness relative to Prilosec® showed only marginal improvements for one particular condition, which affects only a fraction of patients who have acid reflux disease.

As may be appreciated, embodiments of the disclosed technology may be used to reduce the amount of work, friction, and/or associated costs in such clinical trials and post-trial studies. The disclosed technology, for example, may enable data harvesting by independent, unbiased researchers to provide valuable insights so that certain public policy decisions (such as Medicare coverage) may be influenced by the data, rather than by a marketing campaign. Conversely, the disclosed technology may be used for the benefit of drug manufacturers to reduce post-trial study costs while improving the visibility and/or harvestability of the associated data.

Example Use Case 2: Pandemic Response

Clinical trials have been utilized recently to test mRNA-based vaccines for the prevention or reduction of severity of the Covid-19 illness. Results from early-stage trials have shown sufficient safety and efficacy to warrant emergency use authorization even though the long-term side effects of the vaccine may still be unknown. In a typical clinical trial, the data collection process stops at the end of the trial, and valuable long-term outcomes of participants can be extremely difficult to obtain due to privacy regulations.

Certain implementations of the disclosed technology can provide the technical benefit of allowing researchers to track long-term outcomes and conduct post-trial analysis without running afoul of privacy regulations.

Example Use Case 3: Adverse Drug Interactions

One goal of the disclosed technology is to provide a secure and efficient way to reduce or eliminate adverse drug interactions. A significant number of new drugs are introduced to the market every year with an ever-increasing risk for potential drug interactions, which can lead to altered systemic exposure, resulting in disparities in drug response of the other co-administered drugs. Multiple drug courses for therapy carry the risk of adverse interactions, which may result in loss of efficacy. Therefore, it is crucial to assess potential drug interactions and risk-benefit analysis before market approval and during the post-marketing period.

Adverse Drug Reactions (ADRs) are one of the chief causes of morbidity and mortality in health care, costing around $136 billion annually. It has been estimated that nearly 100,000 deaths occur annually from medical errors out of which, about 7,000 deaths occur due to ADRs. A published study (Lazarou J., et al. "Incidence of adverse drug reactions in hospitalized patients: A meta-analysis of prospective studies," AMA 279 1998: 1200-1205) indicates that hospitalized patients have a serious adverse drug reaction with a casualty rate of 0.32%, which means that there are about 2,216,000 serious ADRs in hospitalized patients, causing over 106,000 deaths annually, making ADRs the 4th leading cause of death, before pulmonary disease, diabetes, AIDS, pneumonia, accidents, and automobile deaths. Another study (Gurwitz J H., et al. "Incidence and preventability of adverse drug events in nursing homes," Am J Med 109.2 (2000): 87-94) assessed that over ~350,000 ADRs occur in United States nursing homes every year. These studies point to a huge public health problem that has not been solved to date. Prevention of ADRs is very a crucial part of building a safer healthcare system for society.

Certain implementations of the disclosed technology may provide or aid in pharmacotherapy management and evaluation for managing medication therapy regimens, for example, to maximize patient safety and medication efficacy. Certain implementations may enable coordination of care among providers. Certain implements may be used to improve clinical outcomes, provide regulatory reporting, and or to aid research, learning, or knowledge discovery. Certain implementations of the disclosed technology can provide the basis for a health intervention platform to address health challenges related to medication non-adherence behaviors, predicting and preventing medication non-adherence, identifying and overcoming reasons for non-adherence, identifying risks, or preventing adverse drug interactions.

In a typical prescription drug scenario, a patient may visit with a physician (either physically or virtually) for evaluation of a healthcare issue. Concluding the evaluation, the physician may suggest and/or prescribe medication for the patient. Depending on factors such as safety, side effects, the potential for abuse, etc., the medication may require a prescription, or it may be purchased over-the-counter (OTC) without a prescription. Pharmacists may fill the prescription with the prescribed dose. Due to the sheer number of different brand names and generic medications on the market, there is an inherent complexity involved in managing so many medications, which can further increase the chance of delivering the wrong, medication or dosage.

Certain implementations of the disclosed technology can provide the technical benefit of detecting potential or actual adverse drug reactions so that it can be prevented without running afoul of privacy regulations.

Example Use Case 4: Prescription Drug-Related Abuse Prevention

Another goal of the disclosed technology is to detect prescription drug-related abuse so that it can be prevented. Prescription drug abuse can happen when an individual obtains a prescription medication via a forged prescription, via an unethical provider, or theft. Other situations exist where an individual may visit doctor after doctor until they find one willing to prescribe. This fraud and abuse come at an enormous cost to physicians, hospitals, insurers, and taxpayers. But the greatest cost is a human one—the tens of thousands of lives lost to addiction, and the relatives and friends they leave behind. According to the Centers for Disease Control and Prevention, about 15,000 people die each year from prescription medicine overdoses. And overdoses lead to an additional 1.2 million emergency room visits each year. Opioids are highly addictive medicines that include prescription painkillers and illicit substances such as heroin. Many people get hooked opioids tiller receiving a legitimate prescription following an injury or surgery. They try to obtain more prescriptions for the medicines and may turn to buy heroin on the street if they are unable to get access to prescription opioids.

As prescription opioid use has soared, so has heroin use. In 2012, doctors prescribed 259 million bottles of opioids, one for every adult in the country. Meanwhile, the number of heroin users skyrocketed over the past 15 years. The majority of new heroin users say they were addicted to prescription opioids first.

Certain implementations of the disclosed technology can provide the technical benefit of detecting potential or actual prescription drug-related abuse so that it can be prevented without running afoul of privacy regulations.

In some or all of the example use cases presented above, there are a number of problems that can stem from the requirement that patient or participant data must be deidentitied to remove personally identifiable information (PII). The first issue is that data with scrubbed PII is difficult to sort or combine. A second issue (that further complicates the first issue) is that an individual's complete healthcare data is not (currently) stored in one "master database," but rather, in a plurality data silos. For example, if a subject receives a vaccine booster at a grocery store pharmacy and not at a hospital, it can be extremely difficult to track outcomes at a patient-level since the grocery store pharmacy and the hospital typically silo and isolate their respective patient data. Such siloing of data can prevent healthcare professionals from coordinating patient care, can diminish the value of patient data, and can lead to major (and potentially costly) errors. Certain implementations of the disclosed technology can provide the technical benefit of enabling the sorting, matching, combining, etc., and harvesting a particular individual's healthcare data using different siloed data sources without running afoul of privacy regulations.

Various example embodiments of the disclosed technology now will be described more fully hereinafter with reference to the accompanying drawings, in which some, but not all embodiments of the disclosure are shown. This technology may, however, be embodied in many different forms and should not be construed as limited to the implementations set forth herein; rather, these implementations are provided so that this disclosure will be thorough and complete, and will convey the scope of the disclosed technology to those skilled in the art.

FIG. 1A depicts an example tokenization result using traditional predictive matching methods.

FIG. 1B depicts another example tokenization result using another predictive matching method that generates different token assignments compared to the example tokenization process of FIG. 1A even though the PII data is the same.

FIG. 1C depicts an example tokenization result using an improved tokenization process that utilizes a universal reference database (URD) and unique identifiers for linking and clustering identity information in accordance with certain exemplary implementations of the disclosed technology.

In the data examples shown in FIGS. 1A, 1B, note that the top two rows (Jane vs. Janet) are assigned the same "A" token due to the use of traditional probabilistic matching, for example, to mistakenly conclude that the "t" in the second row is a typographical error (or that one of the names is a common nickname of the other) and that these two rows represent the same person since they have the same date of birth and the same address. However, as depicted in the example tokenization process of FIG. 1C, a Universal Reference Database (LTD) may be utilized to determine that the first two rows represent two separate individuals (such as twins having a similar first name), and two different Patient-Centric Tokens (PCT) may be used to represent the two different individuals.

In the data examples shown in FIGS. 1A, 1B, and 1C, the first and third rows represent a straightforward example of someone who has moved from 123 Main to 123 Oak. Using traditional methods, such as depicted in FIG. 1A, one cannot be confident that the first and third rows correspond to the same person. Thus, in the example shown in FIG. 1A, a separate token is generated for each entity representation of the same person. In contrast, implementations of the disclosed technology, as depicted in FIG. 1C may utilize the URD to have confidence that the first and third-row entity representations represent the same individual who has moved.

FIG. 1D illustrates a scenario where a first trading partner and a second trading partner have different datasets for an individual. In this example illustration, the first trading partner has a name and address information (but no date-of-birth) while the second trading partner has a name and date-of-birth information (hut no address). Using traditional methods, the trading partners can't reliably match or trade associated data with each other for this named individual. However, certain implementations of the disclosed technology may utilize a universal or referential database to solve this issue, as will be further explained below.

As may be evident from the examples above, the disclosed technology may be used to avoid incorrect matching/mismatching of PII to corresponding individuals, thus preventing a medical error or preventing personal healthcare data from being wrongly released. Certain exemplary implementations of the disclosed technology may enable combining data from multiple rows or fields (having different or conflicting data, for example) to produce a single unique token to represent a given individual. Accordingly, the resulting dataset may have improved longitudinal connection to the correct individual and may be far more useful than traditional methods for addressing healthcare needs anchor tracking treatment outcomes.

FIG. 2 illustrates an example tokenization system 200 (and associated process) that can be used to match and/or resolve a universal identifier of an individual based on received personally identifiable information (PII). The system may utilize tokens to de-identify matched data to enable data trading without exposing the individual's PII, in accordance with certain exemplary implementations of the disclosed technology. The term "de-identify" herein means to remove any Protected Health Information (PHI), as defined by HIPAA. Various embodiments of the example tokenization system 200 (and associated process) for different use cases will be discussed below with reference to FIGS. 4-6.

The system 200 can include a main tokenizer 202, which may include an exchange node 204 that enables the secure exchange of data (such as PII data, token data, customer data, subscription control, etc.) with other (remote) exchange nodes (EN) 206. In certain exemplary implementations, the remote exchange nodes 206 may be installed at the various associated locations, including but not limited to computers respectively controlled by Trading Partner A 208, Trading Partner B 210, a Trusted 3$^{rd}$ Party 212, and/or a Customer 214. In certain exemplary implementations, the exchange node 204 and/or the remote exchange nodes 206 may be embodied as software and/or hardware that can connect with the other exchange nodes at various locations to conduct online data trading and data management.

In certain exemplary implementations, the exchange node 204 and/or the remote exchange nodes 206 may utilize a distributed cryptographic protocol for secure communications. In accordance with certain exemplary implementations of the disclosed technology, the exchange node 204 and/or the remote exchange nodes 206 may facilitate data exchange, for example, to deliver to customers and/or trading partners dc-identified tokenization of data, in various specified levels of trusted and/or trustless exchanges.

In accordance with certain exemplary implementations of the disclosed technology, the exchange node 204 and/or the remote exchange nodes 206 may be characterized by a protocol that enables two or more data owners to directly map the modeled identities held in common without the requirement of disclosing identifying information to each other or any third party, as discussed in U.S. Patent Publication No. US20210143985 to Mullin and assigned to Karlsgate LLC, which is incorporated herein by reference as if presented in full.

The system 200 may include or may be in communication with, a Universal Reference Database (URD) 216. The URD 216 may be a (huge) repository that is configured to store universal reference identifiers (such as Patient-Centric Tokens and/or other identifiers including but not limited to device identifiers) that can unambiguously represent the unique identities of individuals (and/or specific devices used by specific individuals). The URD 216, in combination with the processes of the main tokenizer 202, may enable uniquely identifying an individual responsive to receiving and/or a device identifier, for example, PII Data A 218, PII Data B 220, and/or customer data 222 respectively from the Trading Partner A 208, Trading Partner B 210, a Customer 214, and/or a communication device 215. In certain exemplary implementations, information unique to the communication device 215 may be utilized as an identifier. In certain implementations, the communication device 215 may be identified by, one or more of its model number, unique system ID, International Mobile Station Equipment Identity (IMEI) number, International Mobile Subscriber Identity (IMSI) number, a MAC address, an IP address, a SIM ID (ICCID) number, etc. In accordance with certain exemplary implementations of the disclosed technology, identity provisioning using the communication device 215 may be perfomed using techniques including, but not limited to Over-the-Air (OTA) messaging. Certain exemplary implementations of the disclosed technology may utilize one or more of a Mobile Switching Center (MSC), a Visitor Location Register (VLR), a Home Location Register (HLR), an Authentication Center (AUC), and an Equipment Identity Register (EIR) for linking a communication device 215 to an individual. By way of example and not limitation, a communication device 215 may be embodied as a personal computer (PC), a laptop computer, a mobile or mobile device, a smartphone, a tablet computer, a smart watch, a wearable computer, a personal digital assistant (PDA), an MP3 player, a global positioning system (GPS) or device, a video player, a handheld communications device, a gaming device or system, an entertainment system, a vehicle computer system, an embedded system controller, a camera, a remote control, a bar code scanner, a computerized measuring device, an appliance, a consumer electronic device, a workstation, or any combination of these delineated devices, or any other suitable device. In certain example embodiments, the identifying (ID) information unique to the communication device 215 may be a composite value derived or created based on a combination of data provided by, or on behalf of, the communication device 215. For example, the communication device 215 ID can be based on one or more of the following values: user interactions with the device, subscriber identity information stored on a SIM card, a Near Field Communication (NFC) chip, IMEI, network-provided information, a list of web browser plug-ins/add-ons, cookies, user agent, and/or other headers provided by a browser. As will be discussed below, even if received PII data is incomplete or out-of-date, certain exemplary implementations may still uniquely identify the correct individual with higher accuracy than has previously been achievable using traditional methods.

Certain exemplary implementations of the system 200 may include or may be in communication with other databases, such as a data repository 217, which may be used to store other relevant information, including but not limited to safety data, fraud data, geographical data, non-PII data, etc., as will be discussed further with reference to FIG. 3.

The main tokenizer 202 of the system 200 may be utilized to resolve and/or combine data sets to resolve a single universal identifier of an individual. As illustrated in FIG. 2 for example, Trading Partner A 208 may wish to trade certain healthcare (or other) data with Trading Partner B 210. Consider an example scenario where Trading Partner A 208 wants to obtain certain healthcare information from Trading Partner B 210. Trading Partner A 208 has possession of PII Data A 218 with PII fields such as first name, last name, and zip code, and populated with corresponding attribute values. However, Trading Partner B 210 has possession of PII fields populated with attributes/elements/fields that include only a last name and date of birth. The common field attribute of just the last name possessed by both trading partners is not sufficient to provide confidence that data shared directly with each other will correspond with the correct individual(s). The main tokenizer 202, however, may be used to resolve and determine matches among the PII attributes/elements/fields received from the trading partners by utilization of the URD 216, which may contain a more complete set (or all) of the combinations of PII for all individuals. In practice, the URD 216 may store (or have access to) billions of distinct PII combinations, which may represent a given population, such as (but not limited to) the entire US adult population.

In accordance with certain exemplary embodiments, the system 200 shown in FIG. 2 may be utilized to implement a process for trading information among trading partners using a multi-step process, which in certain exemplary implementations, can include the following steps:

Step 1: Trading Partner A 208 shares the list of PII (PII Data A 218) with the main tokenizer 202 (and/or a Trusted $3^{rd}$ Party 212, depending on the use case, as will be further discussed below), and each record may be resolved/matched and assigned an internal token (which in the healthcare application may be a patient-centric token (PCT)). As discussed above, the set of PII elements/fields sent by Trading Partner A 208 may be matched against the superset of elements/fields in the URD 216. In certain implementations, particularly with very incomplete or erroneous data proved by the trading partner, a 100% one-to-one match may not be achievable or required. However, embodiments of the disclosed technology increase the match rate compared with conventional methods.

Step 2: The same process as in Step 1 may be done using PII (PII Data B 220) from Trading Partner B 210. Then variations in the identity data (different zip codes or changed names) that occur within the dataset of either partner or between the datasets of each partner may be resolved and matched to the same universal identifier and thus assigned a common internal PCT.

Step 3: Records in the two data sets may be matched using the PCT. Then all or part of the PII may be removed (de-identifying the datasets) and ePCTs may be generated (for example, by the token generator 224 and/or the PCT transformer) and sent back to the trading partners.

If Trading Partner A 208 provided PII for a Jane Smith with a Main Street address, and Trading Partner B 210 provided PII for a Jane Jones with an Oak Street address, for example, both trading partners may receive the same patient-centric token if the main tokenizes 202 determines (from the URD 216) that Jane Smith and Jane Jones are the same people.

Depending on the use case, there can be situations where only the ePCTs are sent back to trading partners in an order corresponding to the received PII data, but without any further PII. Such information may still be of value to the trading partner(s) since they can use such information to resolve their dataset, and/or to improve and leverage the dataset that another trading partner shared with them.

As illustrated in FIG. 2, the Trusted $3^{rd}$ Party 212 may act as a facilitator of data sharing between the various trading partners 208 210, customer(s) 214, and/or the main tokenizer 202. In certain exemplary implementations, the Trusted $3^{rd}$ Party 212 may provide a data "wall" between the main tokenizer 202 and the trading partners 208 210 and/or customer(s) 214, for example, to further ensure that HIPAA-related PII is not exposed, or that it is not accessible by any entity other than the entity that possessed such information, to begin with. In certain exemplary implementations, the Trusted $3^{rd}$ Party may utilize a lookup table or process to generate ePCTs. As discussed above, the ePCT may provide a secure reference to the identity of a specific person, as expressed by a non-sensitive data element that is undecipherable to any person or organization except for a Trusted $3^{rd}$ Party. In certain exemplary implementations, a set of ePCTs may be created for each potential organization that may receive the tokens so they may be customer- or data partner-specific. The ePCTs can provide stable, repeatable ways of creating a token for a person's identity that is specific to that target organization. In certain example implementations, ePCTs may be accessed and/or used with the possession of a digital key, for example, that can be specific to an organization such that no other organization will have access to these digital keys.

With further reference to FIG. 2, the main tokenizer 202 may include one or more of the following modules: a token generator 224, a PCT transformer 226, and/or a token subscription service 228. In certain exemplary implementations, the token generator 224 may be used to generate a unique token for records that refer to the same individual, for example, so that trading partner data can be internally matched and/or matched with data received from other trading partners. Certain implementations of the main tokenizer 202 may be used to aggregate multiple common identities a universal identifier (such as a PCT).

In certain exemplary implementations, the PCT transformer 226 may be utilized to handle translation among tokens previously generated and received from the trading partners and tokens generated by the main tokenizer 202, as will be further discussed below with reference to FIG. 4.

In accordance with certain exemplary implementations of the disclosed technology, the token subscription service may be used to control the exchange of information between trading partners. For example, when trading partners 208 210 have a valid subscription, the token subscription service 228 may be used to authenticate, control, and/or otherwise facilitate direct trading 230 between trading partners and/or trading through the Trusted $3^{rd}$ Party 212.

Figure 3:
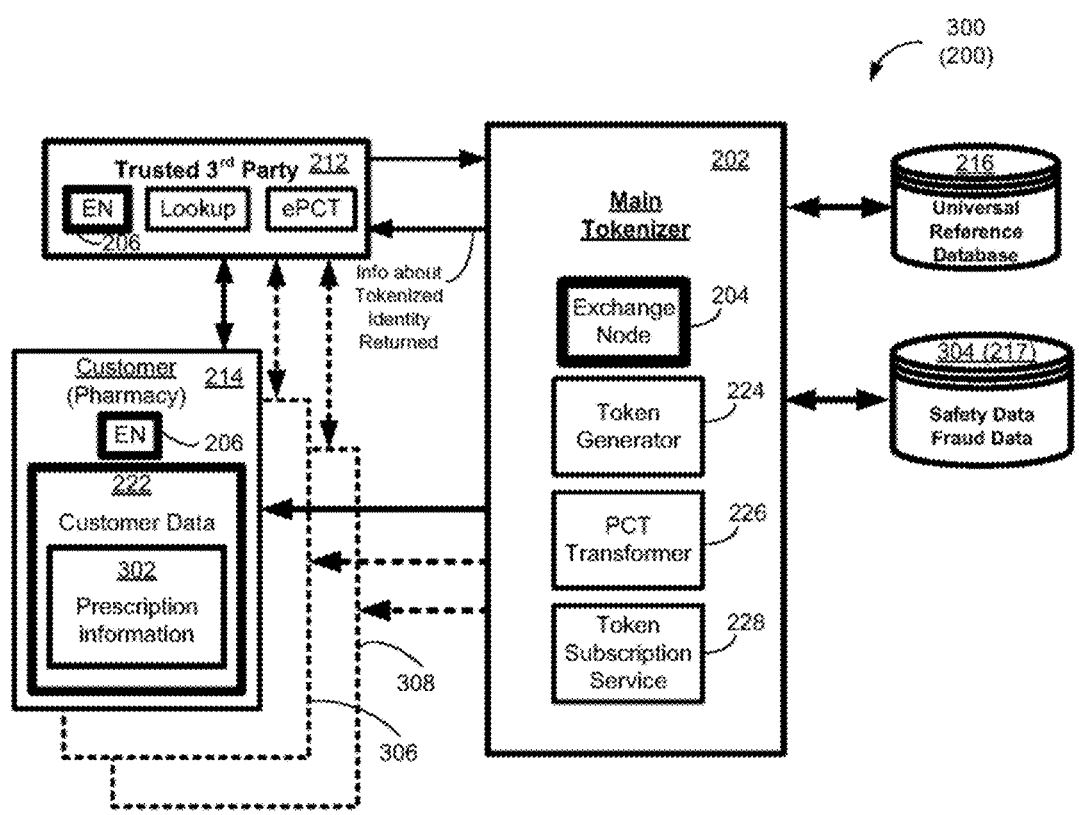
FIG. 3 illustrates an example configuration 300 that can utilize certain components of the example tokenization system 200 (as shown in FIG. 2) for various use cases, such as post-clinical trial tracking, pandemic response evaluation, improving prescription drug safety, detecting prescription drug fraud, etc., in accordance with certain exemplary implementations of the disclosed technology.

FIG. 3 illustrates an example configuration 300 that can utilize certain components of the example tokenization system 200 (as shown in FIG. 2) for improving prescription drug safety and/or detecting prescription drug fraud, in accordance with certain exemplary implementations of the disclosed technology. In this example use case, the customer 214 may be a pharmacy in possession of data 222 that can include prescription information 302 corresponding to prescriptions filled at the pharmacy, including but not limited to the patient PHI, patient PII, current and historical drug prescriptions, insurance information, and doctor information.

Certain implementations of the configuration 300 of the example tokenization system 200 may be in communication with other pharmacies 306 and/or fill centers 308 so that a comprehensive view of a patient's prescription record and activity can be evaluated, for example, to prevent adverse drug interactions and/or to prevent drug prescription-related fraud in a way that does not expose a patient's PII or violate HIPAA laws.

As discussed above with reference to FIG. 2, the main tokenizer 202 may include an exchange node 204 for secure exchange of data (such as PII data, token data, customer data, subscription control, etc.) with the other (remote) exchange nodes (EN) 206 at the pharmacy, fill center, Trusted $3^{rd}$ Party 212, etc.

When a prescription is filled at the pharmacy 214, certain selected prescription information 302 may be securely transmitted to the Trusted $3^{rd}$ Party 212. Upon receipt of the prescription information 302, the Trusted $3^{rd}$ Party 212 may communicate the appropriate information to the Main Tokenizer 202 via the corresponding exchange nodes 206 204. In some implementations, particularly if a patient has had previous prescriptions filled at the pharmacy 214, and/or if a previous token has been generated for the patient, the patient's PII may be replaced with hashed or previously-generated token information (such as an ePCT), which the Trusted $3^{rd}$ Party 212 may forward to the main tokenizer 202 or use to lookup the relevant patient data without requiring the pharmacy 214 to transmit non-secure PII to the Trusted $3^{rd}$ Party 212. Otherwise, if the prescription information 302 corresponds to a new patient having no previous record or token, the pharmacy 214 may securely communicate new patient PII to the Trusted $3^{rd}$ Party 212 via the exchange nodes 206, and the Trusted $3^{rd}$ Party 212 may send this information to the main tokenizer 202 exchange node 204. The main tokenizer 202 may use such information to generate a corresponding PCT using the URD 216, as discussed above with reference to FIG. 2. Again, as discussed above, the Trusted $3^{rd}$ Party 212 may function as an extra layer of security and/or coordination between the pharmacy 214 and the main tokenizer 202.

In accordance with certain exemplary implementations of the disclosed technology, the prescription information 302 sent by the pharmacy 214 to the Trusted $3^{rd}$ Party 212 may also include the specific prescription dose, name, brand, etc., to be fulfilled, and/or any other prescription information associated with the patient. This prescription information 302 may also be transmitted to the main tokenizer 202. A similar process may be carried out by another pharmacy 306, fill center 308, etc. The main tokenizer 202 may retrieve safety and/or fraud data 304 related to the prescription information 302 and may compare the safety data 304 against a comprehensive record of the patient's current and past prescriptions to flag any potential combinations that could create an adverse reaction. Upon detecting any potential adverse reactions, and according to one example implementation, the main tokenizer 202 may provide an alert (via the Trusted $3^{rd}$ Party 212, for example) to notify the pharmacy 214 (and/or prescribing doctor) of the potentially adverse combination, so that the prescription fulfillment may be stopped.

There exist situations particularly involving certain pain medications or other addictive medications) where a so-called "patient" may visit multiple doctors to obtain multiple prescriptions to be filled by different pharmacies for fraudulent abuse or fraudulent selling of the prescription drug. Certain exemplary implementations of the disclosed technology may utilize safety and/or fraud data 304 related to the prescription information 302 and may compare the information against a comprehensive record of the patient's current and past prescriptions (for all participating pharmacies 214, 306, 308 to flag any potential over-the-limit situations (and/or adverse combinations) that could correspond to fraud or abuse (or adverse reactions). Upon detecting any potential fraud or abuse (or dangerous drug combinations), and according to certain exemplary implementations, an alert may be generated and provided (via the Trusted $3^{rd}$ Party 212, for example) to notify the pharmacy 214 (and/or prescribing doctor(s), and/or one or more data sources) of the potential fraud or abuse (or potential adverse reaction), so that the prescription fulfillment may be stopped. Furthermore, certain implementations of the disclosed technology may be similarly utilized to detect when a given doctor is overprescribing medication so that it can be flagged and stopped.

Figure 4:
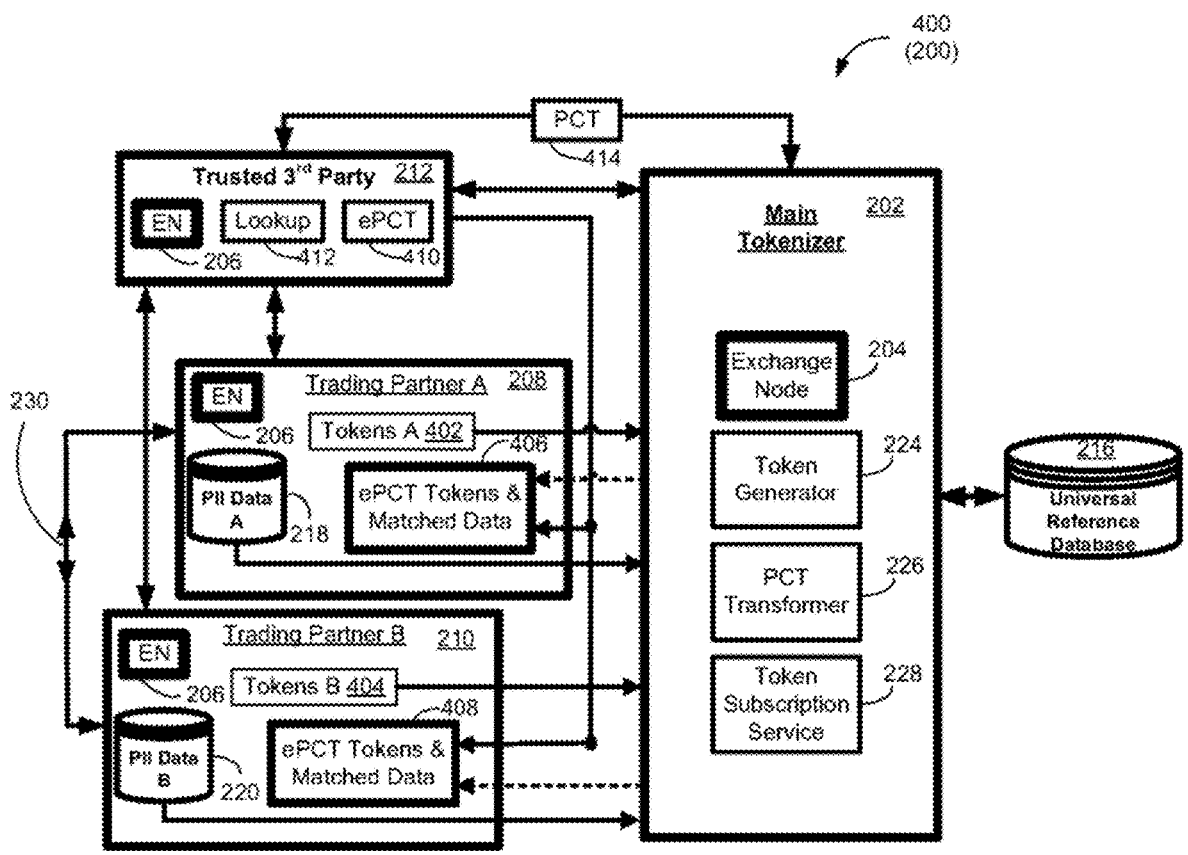
FIG. 4 illustrates an example configuration 400 that can utilize certain components of the example tokenization system 200 (as shown in FIG. 2) to resolve incomplete or mismatched PII data received from trading partners and to match and tokenize the data, in accordance with certain exemplary implementations of the disclosed technology.

FIG. 4 illustrates an example configuration 400 that can utilize certain components of the example tokenization system 200 (as shown in FIG. 2) to resolve incomplete or mismatched PII data 218 220 received from trading partners 208 210 and to match and tokenize the data using the URD 216, in accordance with certain exemplary implementations of the disclosed technology. In certain exemplary implementations, the configuration 400 may enable and/or control direct trading 230 among trading partners 208 210. For example, when trading partners 208 210 have a valid subscription, the token subscription service 228 may be used to authenticate, control, and/or otherwise facilitate direct trading 230 between trading partners and/or trading via the Trusted $3^{rd}$ Party 212.

The example configuration 400 may enable a tokenization process, for example, to aggregate common (but perhaps non-identical) PII data sets 218 220 received from respective trading partners 208 210 to resolve a universal identifier for matching the PII data sets 218 220 with an individual (such as a patient). In certain exemplary implementations, the main tokenizer 202 may create a PCT 414 via the token generator 224 in communication with the URD 216 based on the PII data sets 218 220 received from respective trading partners 208 210. In certain exemplary implementations, the main tokenizer 202 may create the PCT 414 via the token generator 224 in communication with the URD 216 based on (non-patient-centric or other) tokens 402 404 already used by one or more trading partners.

In accordance with certain exemplary implementations of the disclosed technology, the PCT 414 generated by the token generator 224 may be transmitted to the Trusted $3^{rd}$ Party 212 via exchange nodes 204 206. The Trusted $3^{rd}$ Party 212 may generate a corresponding ePCT 410 responsive to receiving the PCT 414. In certain exemplary implementations, the Trusted $3^{rd}$ Party 212 may use a lookup table 412 to retrieve a previously generate ePCT 410 based on the received PCT 414 from the Main Tokenizer 202. As discussed above the ePCT 410 may represent the same individual as the PCT 414, but the ePCT 410 has an additional layer of security. The ePCT 410 is a reference to the identity of a specific person, as expressed by a non sensitive data element that is undecipherable (i.e., not-traceable hack to the original PII). In certain exemplary implementations, the ePCT may be traced back to the PCT, but not to the actual identity—even by a Trusted $3^{rd}$ party unless it is specifically setup to include the ability to do so. Certain ePCTs 410 may be created to be customer or data partner-specific. In certain exemplary implementations, the ePCT 410 may be accessed and/or used with possession of a digital key, for example, that can be specific to an organization such that no other organization will have access to these digital key values.

The example configuration 400 depicted in FIG. 4 may be used to enable the following use case: Trading Partner A 208 may possess tokens 402 corresponding to their own data 218. Trading Partner B 210 may possess tokens 404 corresponding to their own PII data 220. These tokens 402 404 may or may not be created using the same PII 218 210 elements/fields and/or the same tokenization or matching methodology, Trading Partner A 208 and Trading Partner B 210 may want to be able to trade certain data with each other that corresponds to the same individual, hut they might not be able to due to their different PII elements/fields or tokenization or matching methodology. Certain exemplary implementations of the disclosed technology may solve this problem using the following steps:

Step 1: Trading partner A 208 may send their list of tokens 402 and corresponding PII data 218 (used to create the tokens 402) to the main tokenizer and/or to the Trusted $3^{rd}$ Party 212.

Step 2: The main tokenizer 202 may match the PII data 218 against the reference dataset in the URD 216 and may use a universal identifier to create a PCT (or non-industry specific token). Note that this step allows the aggregation across multiple trading partner tokens into a single token (i.e., if the trading partner has separate tokens for Jane Smith at 123 Main and Jane Smith at 123 Oak, as depicted in FIG. 1, both different tokens could be matched to the same PCT).

Step 3: The main tokenizer 202 may then send the original tokens 402 matched to the PCT 414 (or non-industry specific token) to the Trusted $3^{rd}$ Party 212, where the PCT 414 may be replaced with an ePCT 410. The original tokens 402 and corresponding ePCTs 410 may be returned to the Trading Partner A 208. This represents a "crosswalk" allowing Trading Partner A 208 to translate their tokens 402 to an ePCT 410, which can provide significant value and allow utilization of existing token methods used by the trading partner.

Step 4: The same process described above in Steps 1-3 may be used for Trading Partner B 210.

Step 5: Trading Partner A 208 and Trading Partner B 210 can now use their tokens 402 404 to map their respective PII data 218 220 to the ePCT 410, which allows them to trade with each other. This also allows their common customers of Trading Partner A 208 and Trading Partner B 210 to combine (join or link) data sets that each can provide. Therefore, in addition to "data trading," the disclosed technology also makes the data of a vendor more useful to their customers.

In certain exemplary implementations, the Token Subscription Service 228 may be utilized to enable, control, or prevent the above-referenced exchange of data based on a valid subscription by a trading partner.

Trading Partner A 208 and Trading Partner B 210 could trade data directly with each other using their own tokens (without the use of the disclosed technology), however, they would need to have tokens that are based on the same select PII values and the same tokenization and matching methodology. Without the use of the disclosed technology, the trading partners would not have the benefit of the higher coverage and improved longitudinally that aggregates across PII variations and changes in the identity data, such as when a person changes their name or moves. Thus, certain implementations of the disclosed technology provide a significant improvement in the speed and accuracy of the underlying data trading technology while protecting privacy.

In accordance with certain exemplary implementations of the disclosed technology, the universal identifier (and the associated combinations of PII data linked to it) utilized to create the PCTs 414 may be persistent, but the actual token values shared with trading partners may be further hashed or otherwise altered in such a way that they are still longitudinal but are specific to the trading partner or the trade between partners. This would be done to prevent trading partners from "re-using" the token values with other trades or partners.

Figure 5:
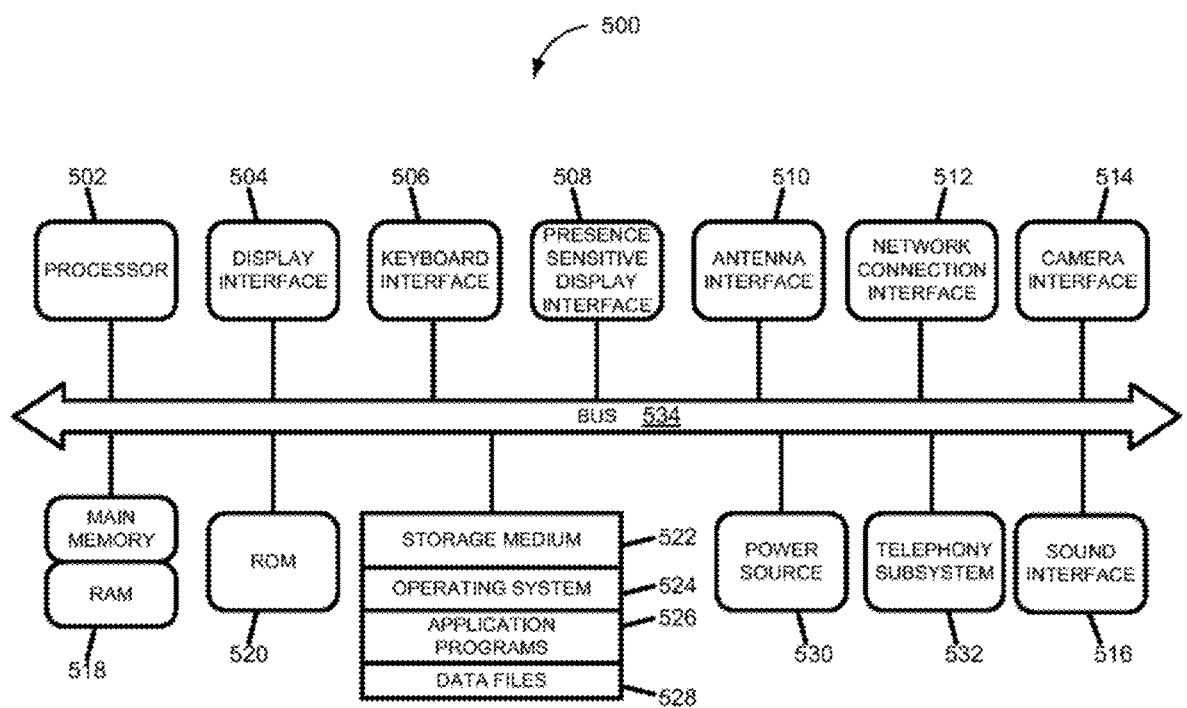
FIG. 5 is a block diagram of a computing device 500 utilized in the system, in accordance with certain example implementations of the disclosed technology.

FIG. 5 depicts a block diagram of an illustrative computing device 500 that may be utilized to enable certain aspects of the disclosed technology. Various implementations and methods herein may be embodied in non-transitory computer-readable media for execution by a processor. It will be understood that the computing device 500 is provided for example purposes only and does not limit the scope of the various implementations of the communication systems and methods.

The computing device 500 of FIG. 5 includes one or more processors where computer instructions are processed. The computing device 500 may comprise the processor 502, or it may be combined with one or more additional components shown in FIG. 5. In some instances, a computing device may be a processor, controller, or a central processing unit (CPU). In yet other instances, a computing device may be a set of hardware components.

The computing device 500 may include a display interface 504 that acts as a communication interface and provides functions for rendering video, graphics, images, and texts on the display. In certain example implementations of the disclosed technology, the display interface 504 may be directly connected to a local display. In another example implementation, the display interface 504 may be configured for providing data, images, and other information for an external/remote display. In certain example implementations, the display interface 504 may wirelessly communicate, for example, via a Wi-Fi channel or other available network connection interface 512 to the external/remote display.

In an example implementation, the network connection interface 512 may be configured as a communication interface and may provide functions for rendering video, graphics, images, text, other information, or any combination thereof on the display. In one example, a communication interface may include a serial port, a parallel port, a general-purpose input and output (GPIO) port, a game port, a universal serial bus (USB), a micro-USB port, a high definition multimedia (HDMI) port, a video port, an audio port, a Bluetooth port, a near-field communication (NFC) port, another like communication interface, or any combination thereof. In one example, the display interface 504 may be operatively coupled to a local display. In another example, the display interface 504 may wirelessly communicate, for example, via the network connection interface 512 such as a Wi-Fi transceiver to the external/remote display.

The computing device 500 may include a keyboard interface 506 that provides a communication interface to a keyboard. According to certain example implementations of the disclosed technology, the presence-sensitive display interface 508 may provide a communication interface to various devices such as a pointing device, a touch screen, etc.

The computing device 500 may be configured to use an input device via one or more of input/output interfaces (for example, the keyboard interface 506, the display interface 504, the presence-sensitive display interface 508, network connection interface 512, camera interface 514, sound interface 516, etc.,) to allow a user to capture information into the computing device 500. The input device may include a mouse, a trackball, a directional pad, a trackpad, a touch verified trackpad, a presence-sensitive trackpad, a presence-sensitive display, a scroll wheel, a digital camera, a digital video camera, a web camera, a microphone, a sensor, a smartcard, and the like. Additionally, the input device may be integrated with the computing device 500 or may be a separate device. For example, the input device may be an accelerometer, a magnetometer, a digital camera, a microphone, and an optical sensor.

Example implementations of the computing device 500 may include an antenna interface 510 that provides a communication interface to an antenna; a network connection interface 512 that provides a communication interface to a network. According to certain example implementations, the antenna interface 510 may utilize to communicate with a Bluetooth transceiver.

In certain implementations, a camera interface 514 may be provided that acts as a communication interface and provides functions for capturing digital images from a camera. In certain implementations, a sound interface 516 is provided as a communication interface for converting sound into electrical signals using a microphone and for converting electrical signals into sound using a speaker. According to example implementations, random-access memory (RAM) 518 is provided, where computer instructions and data may be stored in a volatile memory device for processing by the CPU 502.

According to an example implementation, the computing device 500 includes a read-only memory (ROM) 520 where invariant low-level system code or data for basic system functions such as basic input and output (I/O), startup, or reception of keystrokes from a keyboard are stored in a non-volatile memory device. According to an example implementation, the computing device 500 includes a storage medium 522 or other suitable types of memory (e.g. such as RAM, ROM, programmable read-only memory (PROM), erasable programmable read-only memory (EPROM), electrically erasable programmable read-only memory (EEPROM), magnetic disks, optical disks, floppy disks, hard disks, removable cartridges, flash drives), where the files include an operating system 524, application programs 526 (including, for example, a web browser application, a widget or gadget engine, and or other applications, as necessary) and data files 528 are stored. According to an example implementation, the computing device 500 includes a power source 530 that provides an appropriate alternating current (AC) or direct current (DC) to power components. According to an example implementation, the computing device 500 includes a telephony subsystem 532 that allows the device 500 to transmit and receive sound over a telephone network. The constituent devices and the CPU 502 communicate with each other over a bus 534.

In accordance with an example implementation, the CPU 502 has an appropriate structure to be a computer processor. In one arrangement, the computer CPU 502 may include more than one processing unit. The RAM 518 interfaces with the computer bus 534 to provide quick RAM storage to the CPU 502 during the execution of software programs such as the operating system application programs, and device drivers. More specifically, the CPU 502 loads computer-executable process steps from the storage medium 522 or other media into a field of the RAM 518 to execute software programs. Data may be stored in the RAM 518, where the data may be accessed by the computer CPU 502 during execution. In one example configuration, the device 500 includes at least 128 MB of RAM, and 256 MB of flash memory.

The storage medium 522 itself may include a number of physical drive units, such as a redundant array of independent disks (RAID), a floppy disk drive, a flash memory, a USB flash drive, an external hard disk drive, thumb drive, pen drive, key drive, a High-Density Digital Versatile Disc (HD-DVD) optical disc drive, an internal hard disk drive, a Blu-Ray optical disc drive, or a Holographic Digital Data Storage (HDDS) optical disc drive, an external mini-dual in-line memory module (DIMM) synchronous dynamic random access memory (SDRAM), or an external micro-DIMM SDRAM. Such computer-readable storage media allow the device 500 to access computer-executable process steps, application programs, and the like, stored on removable and non-removable memory media, to off-load data from the device 500 or to upload data onto the device 500. A computer program product, such as one utilizing a communication system may be tangibly embodied in storage medium 522, which may comprise a machine-readable storage medium.

According to one example implementation, the term computing device, as used herein, may be a CPU, or conceptualized as a CPU (for example, the CPU 502 of FIG. 5). In this example implementation, the computing device (CPU) may be coupled, connected, and/or in communication with one or more peripheral devices.

Figure 6:
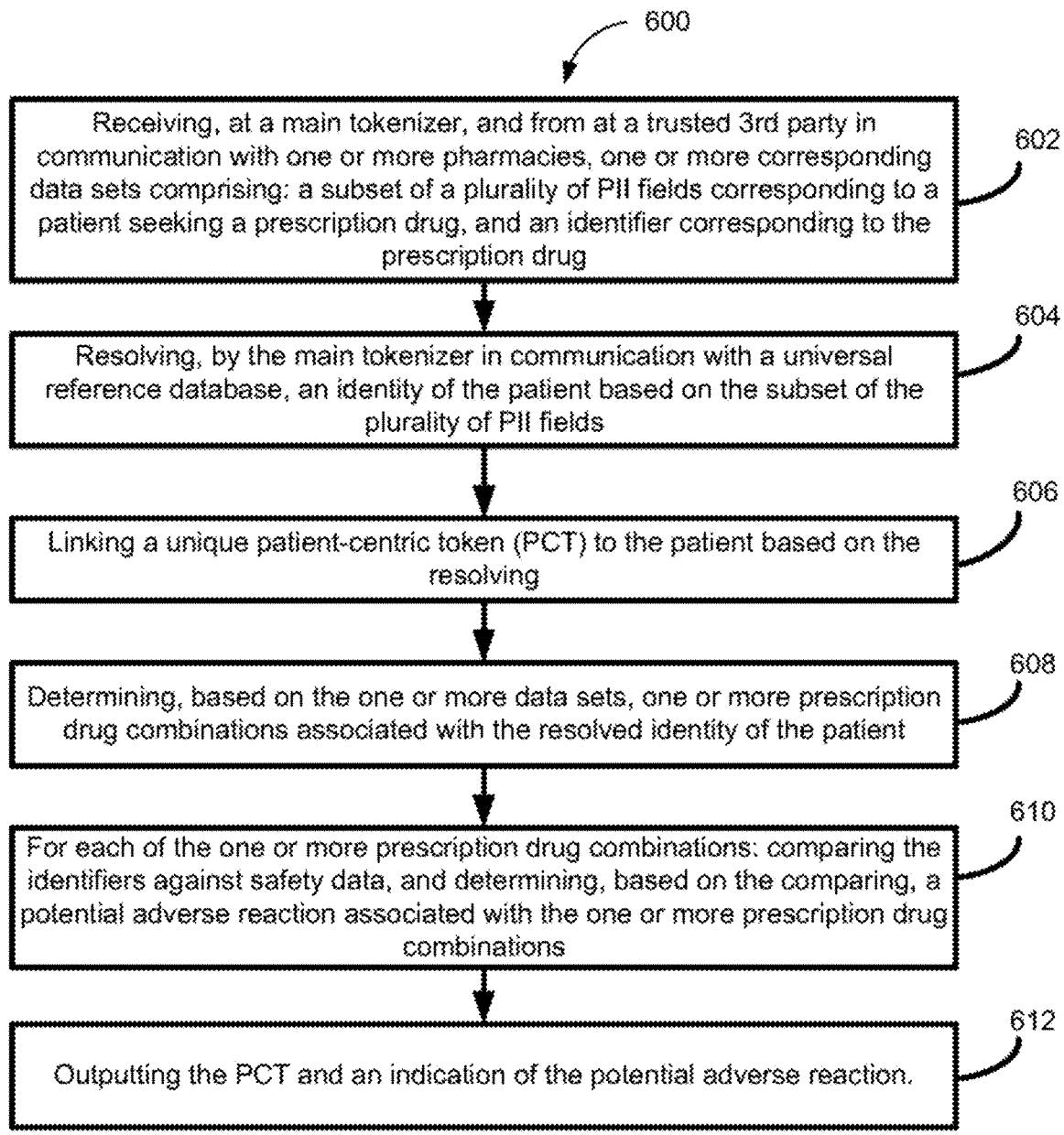
FIG. 6 is a flow diagram of an example method 600 for using the disclosed technology to improve prescription drug safety and/or detect prescription drug fraud, according to certain exemplary implementations of the disclosed technology.

FIG. 6 is a flow diagram of a method 600 for detecting and preventing potential adverse reactions of prescription drug combinations, according to one or more example implementations of the disclosed technology. In block 602, the method 600 includes receiving, at a main tokenizer, and from at a trusted $3^{rd}$ party in communication with one or more pharmacies, one or more corresponding data sets comprising: a subset of a plurality of PII fields corresponding to a patient seeking a prescription drug, and an identifier corresponding to the prescription drug. In block 604, the method 600 includes resolving, by the main tokenizer in communication with a universal reference database, an identity of the patient based on the subset of the plurality of PII fields. In block 606, the method 600 includes linking a unique patient-centric token (PCT) to the patient based on the resolving. In block 608, the method 600 includes determining, based on the one or more data sets, one or more prescription drug combinations associated with the resolved identity of the patient. In block 610, the method 600 includes, for each of the one or more prescription drug combinations: comparing the identifiers against safety data, and determining, based on the comparing, a potential adverse reaction associated with the one or more prescription drug combinations. In block 612, the method 600 includes outputting the PCT and an indication of the potential adverse reaction.

Certain exemplary implementations of the disclosed technology can further include linking, by the trusted $3^{rd}$ party, a non-PII token to the PCT corresponding to the patient. In some implementations, the linking can include generating a new non-PII token when the patient is determined to be a new patient; and saving the new non-PII token in a repository. In some implementations, the linking can include retrieving a previously-generated non-PII token when the patient is determined to be a repeat patient.

Certain exemplary implementations of the disclosed technology can include sending the non-PII token and the indication of the potential adverse reaction to the one or more pharmacies. Certain exemplary implementations of the disclosed technology can include sending one or more of the PCT, an ePCT, and an indication of the potential adverse reaction to one or more of the customer (such as a pharmacy), a doctor, a hospital, a pharmaceutical company, and a trusted $3^{rd}$ party.

In accordance with certain exemplary implementations of the disclosed technology, the identifier corresponding to the prescription drug can include one or more of: an imprint code; a generic name, a brand name, a chemical name, or a recommended international non-proprietary name.

In certain exemplary implementations, the universal identifier may be a persistent identifier.

Figure 7:
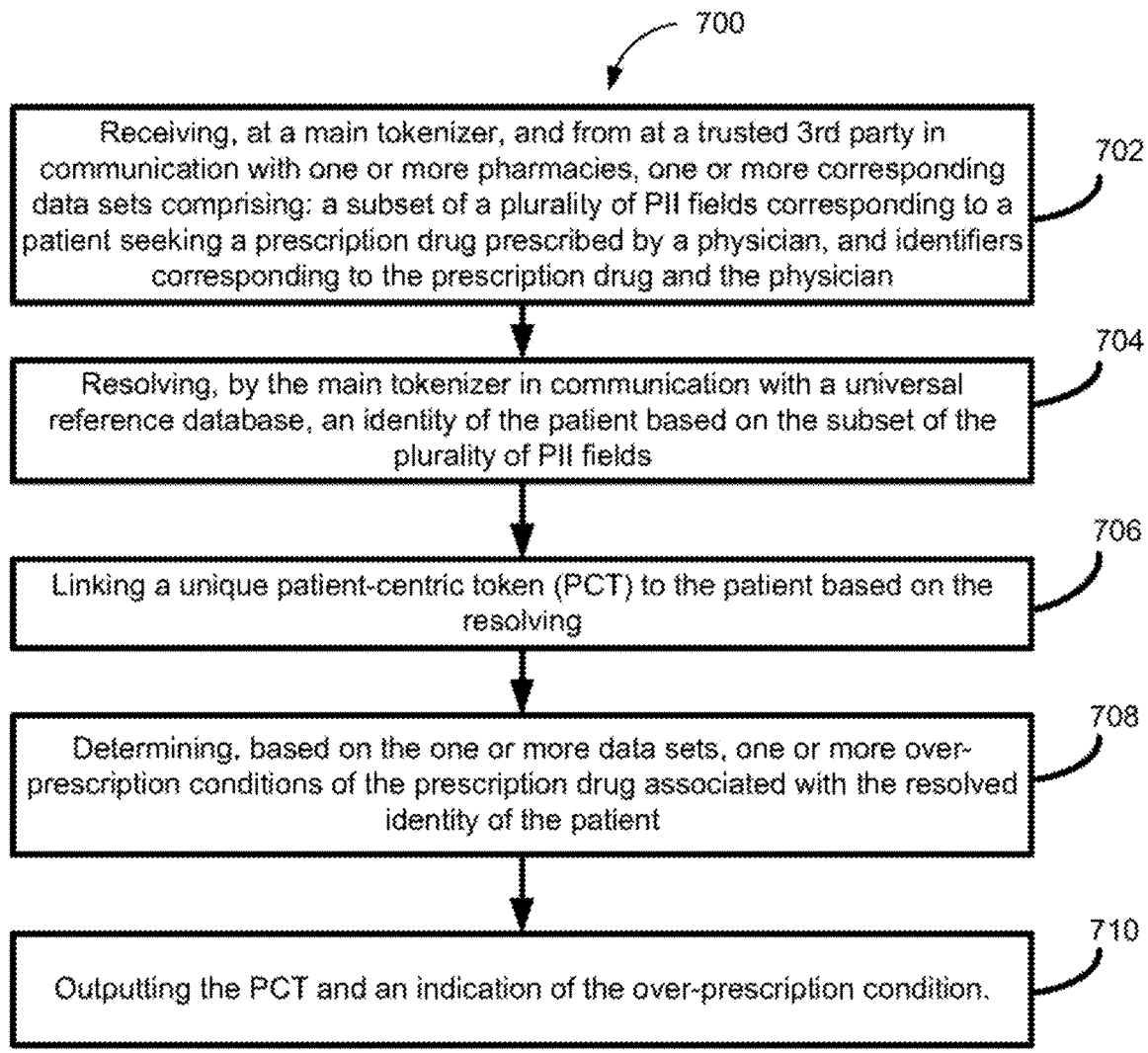
FIG. 7 is a flow diagram of an example method 700, in accordance with certain exemplary implementations of, the disclosed technology.

FIG. 7 is a flow diagram of a method 700 for detecting and preventing prescription drug fraud, according to one or more example implementations of the disclosed technology. In block 702, the method 700 includes receiving, at a main tokenizer, and from at a trusted $3^{rd}$ party in communication with one or more pharmacies, one or more corresponding data sets comprising: a subset of a plurality of PII fields corresponding to a patient seeking a prescription drug prescribed by a physician, and identifiers corresponding to the prescription drug, and the physician.

In block 704, the method 700 includes resolving, by the main tokenizer in communication with a universal reference database, an identity of the patient based on the subset of the plurality of PII fields. In block 706, the method 700 includes linking a unique patient-centric token (PCT) to the patient based on the resolving. In block 708, the method 700 includes determining, based on the one or more data sets, one or more over-prescription conditions of the prescription drug associated with the resolved identity of the patient. In block 710, the method 700 includes outputting the PCT and an indication of the over-prescription condition.

Certain exemplary implementations of the disclosed technology can further include linking, by the trusted $3^{rd}$ party, a non-PII token to the PCT corresponding to the patient. In certain implementations, the linking can include generating a new non-PII token when the patient is determined to be a new patient and saving the new non-PII token in a repository. In certain exemplary implementations, the linking can include retrieving a previously-generated non-PII token when the patient is determined to be a repeat patient.

Certain exemplary implementations of the disclosed technology can include sending the non-PII token and the indication of the over-prescription condition to the one or more pharmacies. Certain exemplary implementations of the disclosed technology can include sending one or more of the PCT, an ePCT, and an indication of the over-prescription condition to one or more of the customer (such as a pharmacy), a doctor, a hospital, a pharmaceutical company, and a trusted $3^{rd}$ party.

In certain exemplary implementations, the identifier corresponding to the prescription drug can include one or more of an imprint code; a generic name, a brand name, a chemical name, or a recommended international non-proprietary name.

Figure 8:
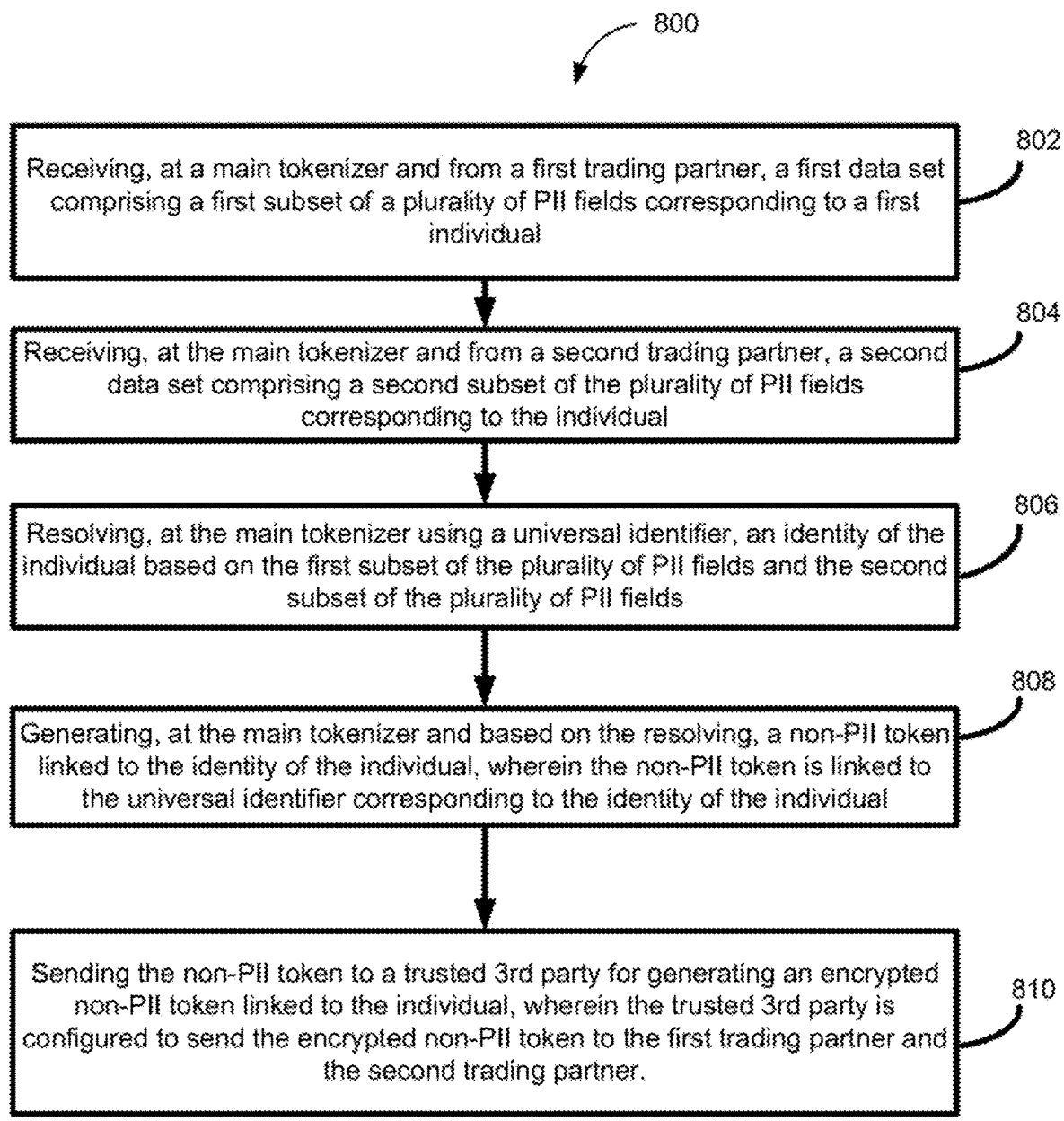
FIG. 8 is a flow diagram of an example method 800, in accordance with certain exemplary implementations of the disclosed technology.

FIG. 8 is a flow diagram of a method 800 for facilitating data sharing among trading partners while protecting patient privacy, according to an example implementation of the disclosed technology. In block 802, the method 800 includes receiving, at a main tokenizer and from a first trading partner, a first data set comprising a first subset of a plurality of PII fields corresponding to an individual. In block 804, the method 800 includes receiving, at the main tokenizer and from a second trading partner, a second data set comprising a second subset of the plurality of PII fields corresponding to the individual. In block 806, the method 800 includes resolving, at the main tokenizer using a universal identifier, an identity of the individual based on the first subset of the plurality of PII fields and the second subset of the plurality of PII fields. In block 808, the method 800 includes generating, at the main tokenizer and based on the resolving, a non-PII token linked to the identity of the individual, wherein the non-PII token is linked to the universal identifier corresponding to the identity of the individual. In block 810, the method 800 includes sending the non-PII token to a trusted 3$^{rd}$ party for generating an encrypted non-PII token linked to the individual, wherein the trusted 3$^{rd}$ party is configured to send the encrypted non-PII token to the first trading partner and the second trading partner. Certain exemplary implementations of the disclosed technology can include sending one or more of a PCT, an ePCT, a non-PII token, and an encrypted non-pII token to one or more trading partners and/or one or more customers.

Figure 9:
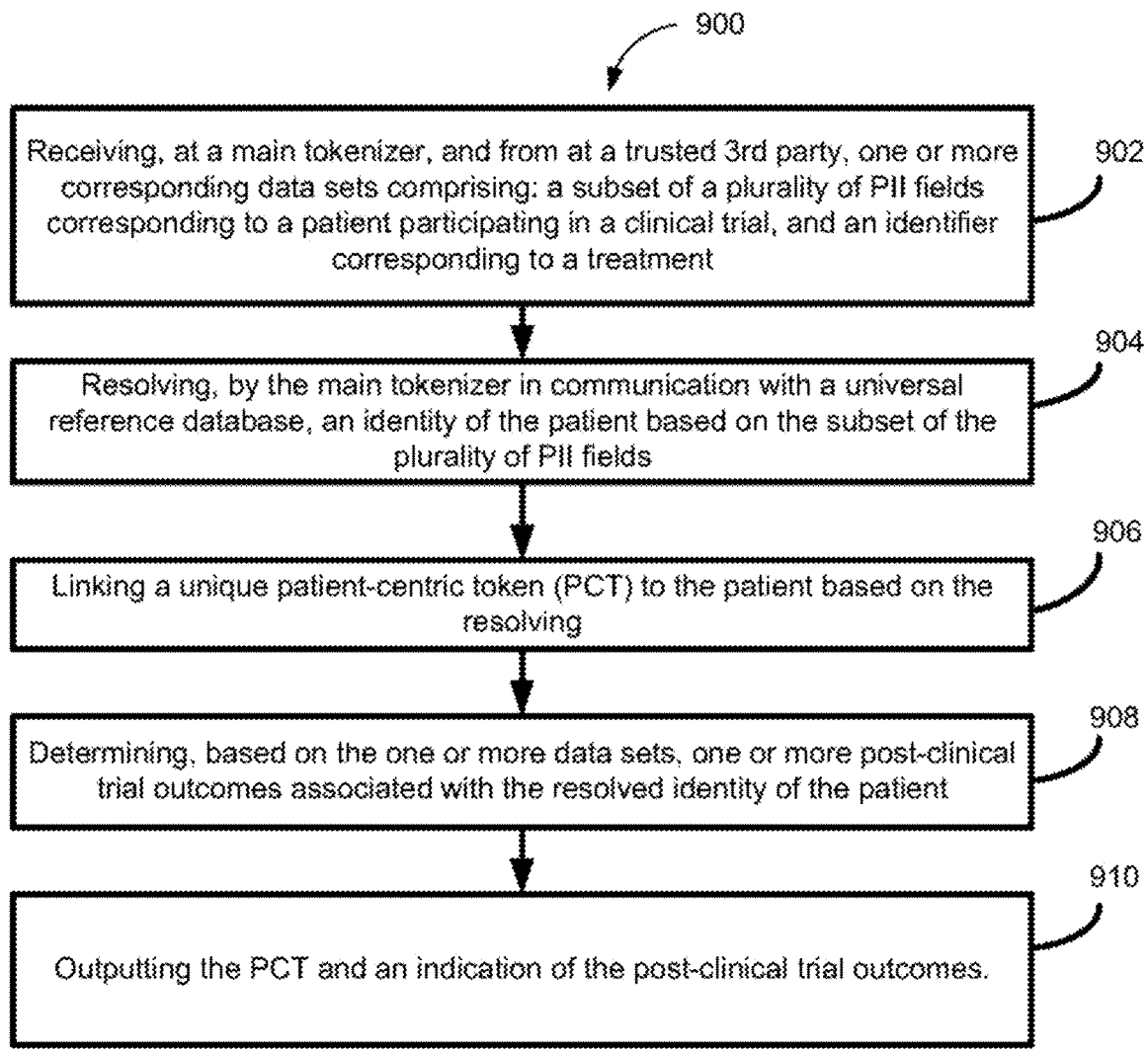
FIG. 9 is a flow diagram of an example method 900, in accordance with certain exemplary implementations of the disclosed technology.

FIG. 9 is a flow diagram of a method 900 for tracking long-term outcomes of patients participating in a clinical trial, according to one or more example implementations of the disclosed technology. In block 902, the method 900 includes receiving, at a main tokenizer, and from at a trusted 3$^{rd}$ party, one or more corresponding data sets comprising: a subset of a plurality of PII fields corresponding to a patient participating in a clinical trial, and an identifier corresponding to a treatment. In block 904, the method 900 includes resolving, by the main tokenizer in communication with a universal reference database, an identity of the patient based on the subset of the plurality of PII fields. In block 906, the method 900 includes linking a unique patient-centric token (PCT) to the patient based on the resolving. In block 908, the method 900 includes determining, based on the one or more data sets, one or more post-clinical trial outcomes associated with the resolved identity of the patient. In block 910, the method 900 includes outputting and an indication of the post-clinical trial outcomes. Certain exemplary implementations of the disclosed technology can include sending one or more of the PCT, an ePCT, and an indication of a post-clinical trial outcome to one or more of a doctor, a hospital, a pharmaceutical company, and a trusted 3$^{rd}$ party.

Figure 10:
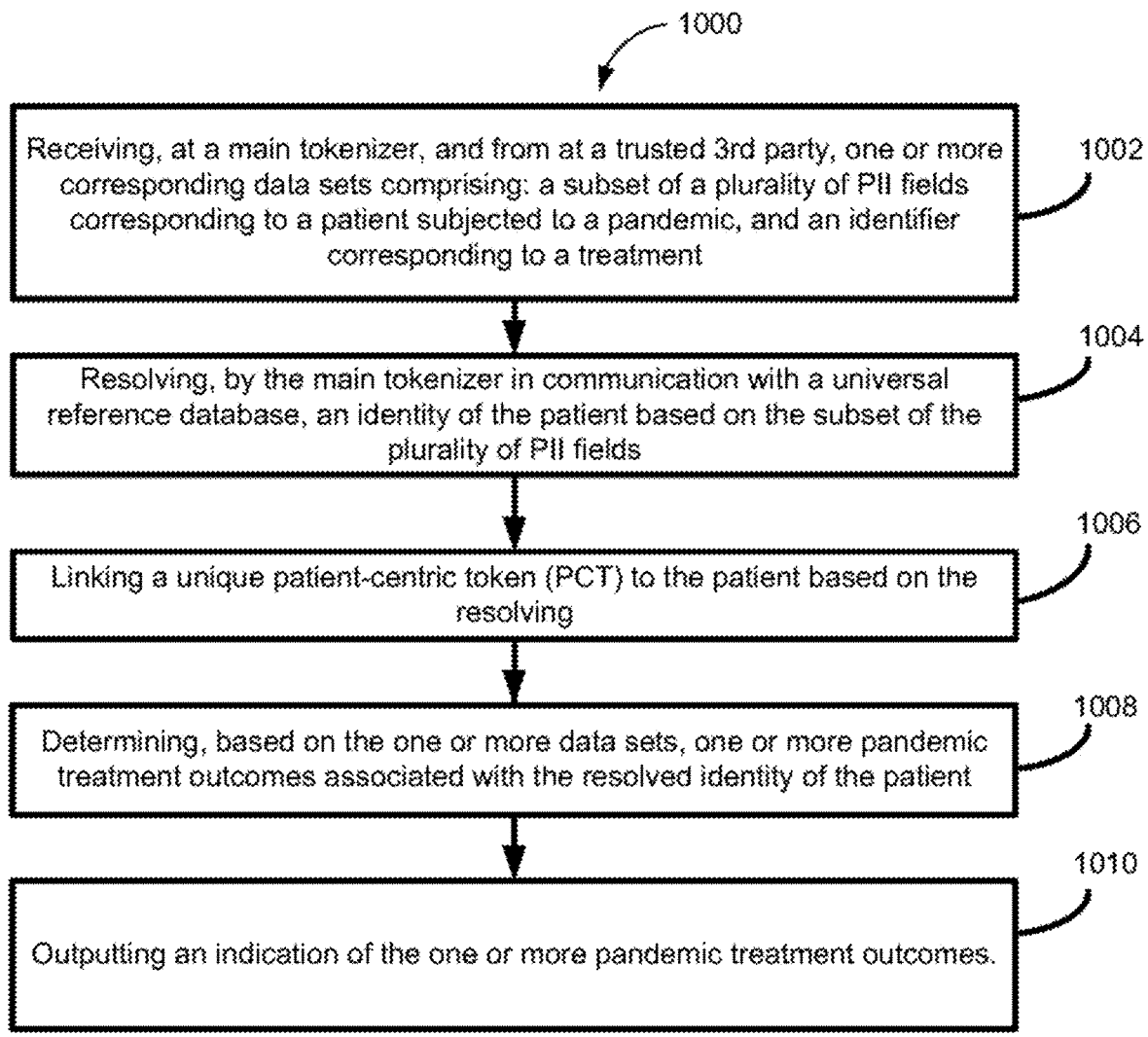
FIG. 10 is a flow diagram of an example method 1000, in accordance with certain exemplary implementations of the disclosed technology.

FIG. 10 is a flow diagram of a method 1000 for tracking pandemic treatment outcomes of patients subjected to a pandemic, according to one or more example implementations of the disclosed technology. In block 1002, the method 1000 includes receiving, at a main tokenizer, and from at a trusted 3$^{rd}$ party, one or more corresponding data sets comprising: a subset of a plurality of PII fields corresponding to a patient subjected to a pandemic, and an identifier corresponding to a treatment. In block 1004, the method 1000 includes resolving, by the main tokenizer in communication with a universal reference database, an identity of the patient based on the subset of the plurality of PII fields. In block 1006, the method 1000 includes linking a unique patient-centric token (PCT) to the patient based on the resolving. In block 1008, the method 1000 includes determining, based on the one or more data sets, one or more pandemic treatment outcomes associated with the resolved identity of the patient. In block 910, the method 900 includes outputting the PCT and an indication of the one or more pandemic treatment outcomes. Certain exemplary implementations of the disclosed technology can include sending one or more of the PCT, an ePCT, and an indication of the one or more pandemic treatment outcomes to one or more of the customer (such as a pharmacy), a doctor, a hospital, a pharmaceutical company, a trading partner, and a trusted 3$^{rd}$ party.

In certain exemplary implementations, the non-PII token is a patient-centric token (PCT) and the encrypted non-PII token is an ePCT.

Certain exemplary implementations of the disclosed technology can further include facilitating an exchange of the first subset of the plurality of PII fields and the second subset of the plurality of PII fields between the first trading partner and the second trading partner based on the non-PII token. In some implementations, facilitating the exchange of the first subset of the plurality of PII fields and the second subset of the plurality of PII fields between the first trading partner and the second trading partner is further based on de-identified matched data.

In certain exemplary implementations, the first subset is the same as the second subset. In certain exemplary implementations, the first subset differs from the second subset.

According to an exemplary implementation of the disclosed technology, the non-PII token is linked to the universal identifier without requiring an SSN of the individual.

In certain exemplary implementations, one or more variations of PII in the first subset and the second subset is resolved to the same universal identifier.

In certain exemplary implementations, generating the non-PII token is based on one or more key identifying attributes/elements/fields comprising one or more of: first name, last name, address, city, state, zip, DOB, SSN, gender name, or a portion of any of these fields (e.g., first initial of first name, house number, ZIP3, Last 4 of SSN, Year of Birth) or phonetic representation of these fields (e.g., Soundex of last name). In certain exemplary implementations, the de-identification and ability to aggregate de-identified identities may focus on a device (such as a communication device 215 as discussed above with reference to FIG. 2) and not necessarily on a patient. In these exemplary implementations, computer, communication, Internet of Things, or other device information such as a MAC address, IP address, SIM ID #, and/or the like may be utilized as one or more identifying attributes for a communication device (such as the communication device 215 depicted in FIG. 2). One exemplary implementation of the disclosed technology may be utilized to de-identify person's identity. Another exemplary implementation may be utilized to de-identify a person's communication device. Yet another exemplary implementation may de-identify a communication device that is used by a do-identified person. In accordance with certain exemplary implementations, layers of of de-identification may be utilized to prevent (or reduce the risk) of PII being released to unauthorized entities.

In accordance with certain exemplary implementations of the disclosed technology, identifying attributes may further include (or be derived from) one or more of: phone number, fax number, email address, medical record number, health plan beneficiary number, account number, certificate, or license number, vehicle identifier, device identifier, web URL, Internet Protocol (IP) address, biometric identification, photographs full-face photographs, and/or any other unique identifying characteristic.

In certain exemplary implementations, the universal identifier is longitudinally consistent and based on comprehensive knowledge of substantially an entire population of people.

According to certain exemplary embodiments, any of the methods described herein can include receiving, at the main tokenizer and from the first trading partner, the non-PII token and the first subset of the plurality of PII fields corresponding to the individual;

According to certain exemplary embodiments, any attic methods described herein can include receiving, at the main tokenizer and from the second trading partner, the non-PII token and the second subset of the plurality of RII fields corresponding to the individual;

Certain exemplary implementations of the disclosed technology can include generating, at the main tokenizer, and using the universal identifier, aggregated de-identified data corresponding to the individual based on the first subset of the plurality of PII fields, the second subset of the plurality of PII fields, and the non-PII token. Certain exemplary implementations of the disclosed technology can include sending, to the first trading partner and the second trading partner, the non-PII token, and the aggregated de-identified matched data corresponding to the individual.

Some implementations can include generating de-identified matched data corresponding to the individual; and sending, to the first trading partner and the second trading partner, the non-PII token, and the de-identified matched data corresponding to the individual.

Thus, certain implementations of the disclosed technology may be used to match different PII data among trading partners using the main tokenizer, and corresponding tokens may be sent back to the trading partners (either directly or via a trusted $3^{rd}$ party) so that the trading partners can link the tokens back to their respective PII data in a way that then allows data trading for the same individual(s) even though the trading partners have different PII data for the individual(s).

In certain aspects of the disclosed technology, the patient-centric token may rely on the non-obvious use of a reference data set (as a third data set) to create a single set of tokens that act as a "Rosetta stone" across different combinations and changing values of PII used to create tokens. Patient-centric (or non-industry-specific) tokens may be created and then used to match data using automated methods. Certain implementations may utilize automation of the reference data set. The use of the reference data for both the "direct" method of tokenizing and matching data plus the ability to use the reference data to create "crosswalks" between existing tokens and patient-centric (or non-industry specific) tokens are non-obvious ways to maximize the utility of the disclosed technology.

Example implementations of the disclosed technology can utilize special-purpose computing systems and custom query language(s) in the processes described herein to provide meaningful results, as may be necessitated due to the sheer amount of data that needs to be tracked and analyzed.

Certain example implementations of the disclosed technology provide tangible improvements in computer processing speeds, memory utilization, and/or programming languages. Such improvements provide certain technical contributions that can enable the detection of relationships among individuals. In certain example implementations, the improved computer systems disclosed herein may enable an analysis of an entire population, such as all known persons in the United States, together with associated PII. The computation of such a massive amount of data, at the scale required to provide effective outlier detection and information, has been enabled by the improvements in computer processing speeds, memory utilization, and/or programming language as disclosed herein. Those with ordinary skill in the art may recognize that traditional methods such as human activity, pen-and-paper analysis, or even traditional computation using general-purpose computers and/or off-the-shelf software, are not sufficient to provide the level of data processing for effective relationship linking. As disclosed herein, the special-purpose computers and special-purpose programming languages) disclosed herein can provide improved computer speed and/or memory utilization that provides an improvement in computing technology, thereby enabling the disclosed inventions.

One of the issues that have plagued previous "relationship determination" solutions involving massive data sets is the extremely long run times and the large amount of memory/disk space required. One of the technical solutions provided by the technology disclosed herein concerns the enablement and efficiency improvement of computer systems and software to process-related data and to provide the desired data in a reasonable amount of time. Certain example implementations of the disclosed technology may be utilized to increase the efficiency of the tokenization process.

Determining relationships among records, for example, can follow the classical n-squared process for both time and disk space. According to an example implementation of the disclosed technology, lightweight self-joins may be utilized, for example, in generating Enterprise Control Language (ECL). But disk-space utilization might still be high. Certain example implementations of the disclosed technology may enable a core join to be split into parts, each of which is persisted. This has the advantage of breaking a potentially very long join into n parts while allowing others a time slice. This has the effect of reducing disk consumption by a factor of n, provided the eventual links are fairly sparse. In terms of performance, it should be noted that if n can be made high enough that the output of each join does not spill to disk, the relationship calculation process may have significantly faster performance.

In accordance with certain example implementations, linking of records may be performed by certain additional special programming and analysis software. For example, record linking fits into a general class of data processing known as data integration, which can be defined as the problem of combining information from multiple heterogeneous data sources. Data integration can include data preparation steps such as parsing, profiling, cleansing, normalization, and parsing and standardization of the raw input data prior to record linkage to improve the quality of the input data and to make the data more consistent and comparable (these data preparation steps are sometimes referred to as ETL or extract, transform, load).

Data profiling, data hygiene, and data source consistency checking, while key components of the record linking process, have their own value within the data integration process and may be utilized herein for leverage even when record linking is not a necessary part of a particular data work unit. Implementations of the disclosed technology may utilize concepts such as term specificity to determine the relevancy/weight of a particular field in the scope of the linking process, and a mathematical model based on the input data, rather than the need for hand-coded user rules, which may be key to the overall efficiency of the method.

In accordance with an example implementation of the disclosed technology, and as discussed above, a persistent data structure may be utilized as a part of splitting a core join, for example, to increase the performance of the computer processor and/or to reduce the disc/memory utilization requirements in determining relationships among records. The persistent data structure, according to certain example implementations of the disclosed technology, is a data structure that preserves the previous version of itself when it is modified. Such data structures may be effectively immutable, as their operations do not update the structure in place, but instead may yield a new updated structure. Certain example implementations may utilize a meld or merge operation that can create a new version from two previous versions. In certain example implementations, the persistent data structure(s) can also be created using in-place updating of data and these may, in general, use less time or storage space than their purely functional counterparts. In certain example implementations, persistence can be achieved by simple copying. Certain example implementations of the disclosed technology exploit a similarity between the new and old versions to share structure between versions.

Certain exemplary implementations of the disclosed technology may update and/or edit PCTs on a regular basis (such as daily, weekly, as-needed, etc.) to reflect splits, joins, changes in identity, changes in confidence values, etc. However, in some instances, such edits can become messy or cumbersome, and recreating/rebuilding the PCTs may be desirable. In certain exemplary implementations, the PCTs may be destroyed (or invalidated) and recreated/rebuilt on a regular basis (such as monthly) to help promote the integrity of the results. Such periodic destruction/recreation of the PCTs may have a benefit of an added layer of security that may further reduce exposure of PII. In accordance with certain exemplary implementations of the disclosed technology, the main tokenizer may manage two sets of PCTs: the current set and a previous set—so that the associated data is available even during the rebuild process.

In accordance with an example implementation of the disclosed technology, input information associated with an individual may be processed, weighted, scored, etc., for example, to disambiguate the information. Certain implementations, for example, may utilize one or more input data fields to verify or correct other input data fields.

According to certain example implementations of the disclosed technology, different modeling approaches may be utilized for implementing trust scores according to various identifiers and depending on the available data, desired accuracy, and/or time or computing constraints.

Certain example implementations of the disclosed technology may provide the following technical benefits and/or technical functions: both online and offline data at tributes/elements/fields may be utilized together to form a dynamic and unique persona identifier (token) that is anonymized; the generative identity resolution process may be driven by real-world digitized interactions, not just data mapping to fields; a digital identity graph, leveraging machine learning, may connect the disparate online and offline attributes/elements/fields and express them as one unique persona identifier that is anonymized; complete anonymity is ensured with both the persona identifiers and underlying data attributes/elements/fields; the system is built upon tokenized, encrypted identity attributes/elements/fields that cannot be hacked or reversed into personally identifiable information (PII); a view of a persona identity and attributes/elements/fields may be provided through the merging of the offline and online data; a consistent, universal, and frictionless approach may be utilized across consumer touchpoints spanning new account openings, login transactions, and payment transactions.

Given that users often have multiple assets of each class e.g., different private emails, work emails, lived in different homes, the concept of tokenized identifiers may only be as useful as it can create a singular entity that strongly correlates with the individual. Without such correlation, there may be no information gain and value beyond the single-tracked attribute.

As used herein, the terms "data," "content," "information," and similar terms may be used interchangeably to refer to data capable of being transmitted, received, and/or stored in accordance with the disclosed technology. Thus, the use of any such terms should not be taken to limit the spirit and scope of the present disclosure. Further, where a computing device is described herein to receive data from another computing device, it will be appreciated that the data may be received directly from another computing device or may be received indirectly via one or more intermediary computing devices, such as, for example, one or more servers, relays, routers, network access points, base stations, hosts, and/or the like, sometimes referred to herein as a "network." Similarly, where a computing device is described herein to send data to another computing device, it will be appreciated that the data may be sent directly to another computing device or may be sent indirectly via one or more intermediary computing devices, such as, for example, one or more servers, relays, routers, network access points, base stations, hosts, and/or the like.

As used herein, the terms "human identity," "user," "client," "consumer," and "patient" may be used interchangeably to refer, without limitation, to a human, client, customer, purchaser, shopper, user and the like who may be using any number of client devices and/or online identities to receive and interact with networked digital content.

Methods, apparatuses, and computer program products of the present disclosure may be embodied by any of a variety of devices. For example, the method, apparatus, and computer program product of an example embodiment may be embodied by a networked device, such as a server or other network entity, configured to communicate with one or more devices, such as one or more client devices. Additionally, or alternatively, the computing device may include fixed computing devices, such as a personal computer or a computer workstation. Still, further, example embodiments may be embodied by any of a variety of mobile devices, such as a portable digital assistant (PDA), mobile telephone, smartphone, laptop computer, tablet computer, wearable, or any combination of the aforementioned devices.

As will be appreciated, any such computer program instructions and/or another type of code may be loaded onto a computer, processor, or other programmable apparatus's circuitry to produce a machine, such that the computer, processor, or other programmable circuitry that executes the code on the machine creates the means for implementing various functions, including those described herein.

It is also noted that all or some of the information presented by the example displays discussed herein can be based on data that is received, generated, and/or maintained by one or more components of apparatuses herein. In some embodiments, one or more external systems (such as a remote cloud computing and/or data storage system) may also be leveraged to provide at least some of the functionality discussed herein.

As described above and as will be appreciated based on this disclosure, embodiments of the present disclosure may be configured as methods, mobile devices, backend network devices, and the like. Accordingly, embodiments may comprise various means including entirely of hardware or any combination of software and hardware. Furthermore, embodiments may take the form of a computer program product on at least one non-transitory computer-readable storage medium having computer-readable program instructions (e.g., computer software) embodied in the storage medium. Any suitable computer-readable storage medium may be utilized including non-transitory hard disks, CD-ROMs, flash memory, optical storage devices, or magnetic storage devices.

Embodiments of the subject matter and the operations described herein can be implemented in digital electronic circuitry, or computer software, firmware, or hardware, including the structures, disclosed in this specification and their structural equivalents, or combinations of one or more of them. Embodiments of the subject matter described herein can be implemented as one or more computer programs, i.e., one or more modules of computer program instructions encoded on the computer storage medium for execution by, or to control the operation of, information/data processing apparatus. Alternatively, or in addition, the program instructions can be encoded on an artificially-generated propagated signal, e.g., a machine-generated electrical, optical, or electromagnetic signal, which is generated to encode information/data for transmission to suitable receiver apparatus for execution by an information/data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described herein can be implemented as operations performed by an information/data processing apparatus on information/data stored on one or more computer-readable storage devices or received from other sources.

The terms "data processing apparatus," "computing devices," and "mobile computing devices" encompass all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field-programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various computing model infrastructures, such as web services, distributed computing, and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or another unit suitable for use in a computing environment. A computer program may, but need not, correspond to a file in a file system. A program can be stored in a portion of a file that holds other programs or information/data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network.

The processes and logic flow described herein can be performed by one or more programmable processors executing one or more computer programs to perform actions by operating on input information/data and generating output. Processors suitable for the execution of a computer program include, by way of example, both general and special purpose microprocessors, and one or more processors of any kind of digital computer. Generally, a processor will receive instructions and information/data from a read-only memory or a random-access memory, or both. The essential elements of a computer are a processor for performing actions in accordance with instructions and one or more memory devices for storing instructions and data. Generally, a computer will also include, or be operatively coupled to receive information/data from or transfer information/data to, or both, one or more mass storage devices for storing data, e.g., magnetic, magneto-optical disks, or optical disks. However, a computer need not have such devices. Devices suitable for storing computer program instructions and information/data include all forms of non-volatile memory, media, and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described herein can be implemented on a computer having a display device, e.g., a CRT (cathode ray tube) or LCD (liquid crystal display) monitor, for displaying information/data to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described herein can be implemented in a computing system that includes a back-end component, e.g., as an information/data server, or that includes a middleware component, e.g., an application server, or that includes a front-end component, e.g., a client computer having a graphical user interface or a web browser through which a user can interact with an implementation of the subject matter described herein, or any combination of one or more such back-end, middleware, or front-end components. The components of the system can be interconnected by any form or medium of digital information/data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship with each other. In some embodiments, a server transmits information/data (e.g., an HTML page) to a client device (e.g., for purposes of displaying information/data to and receiving user input from a user interacting with the client device). Information/data generated at the client device (e.g., a result of the use interaction) can be received from the client device at the server.

As utilized herein, the term "or" is used herein in both the alternative and conjunctive sense, unless otherwise indicated. The terms "illustrative" and "exemplary" are used to be examples with no indication of quality level. Like numbers refer to like elements throughout.

While this specification contains many specific implementation details, these should not be construed as limitations on the scope of any disclosures or of what may be claimed, but rather as descriptions of features specific to embodiments of particular disclosures. Certain features that are described herein in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated with a single software product or packaged into multiple software products.

Thus, particular embodiments of the subject matter have been described. Other embodiments are within the scope of the following claims. In some cases, the actions recited in the claims can be performed in a different order and still achieve desirable results. Also, the processes depicted in the accompanying figures do not necessarily require the particular order shown, or sequential order, to achieve desirable results. In certain implementations, multitasking and parallel processing may be advantageous.

Many modifications and other embodiments of the disclosures set forth herein will come to mind to one skilled in the art to which these disclosures pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims, Although specific terms are employed herein, they are used in a generic and descriptive sense only and not for purposes of limitation.

What is claimed is:

1. A computer-implemented method for detecting and preventing potential adverse reactions of prescription drug combinations, the method comprising:

receiving, at a main tokenizer, and from a trusted $3^{rd}$ party in communication with one or more pharmacies, one or more corresponding data sets comprising:
  a subset of a plurality of personally identifiable information (PII) fields corresponding to a patient seeking a prescription drug; and
  a drug identifier corresponding to the prescription drug;
determining, with one or more computer processors, relationships among the subset of the plurality of PII fields and the drug identifier by:
  creating a core join data structure with at least a portion of all available patient information;
  splitting the core join data structure into persisted parts, wherein the persisted parts are configured for updating a shared structure between versions in memory to reduce disk utilization; and
  updating the shared structure between the versions in the memory;
resolving, by the main tokenizer in communication with a universal reference database (URD) and based on the updated shared structure, an identity of the patient based on the subset of the plurality of PII fields and a persistent universal identifier corresponding to the patient;
linking a unique patient-centric token (PCT) to the patient based on the resolving;
determining, based on the one or more data sets, one or more prescription drug combinations associated with the resolved identity of the patient;
for each of the one or more prescription drug combinations:
  comparing the drug identifier against safety data;
  determining, based on the comparing, a potential adverse reaction associated with the one or more prescription drug combinations; and
outputting the PCT and an indication of the potential adverse reaction.

2. The computer-implemented method of claim 1, further comprising linking, by the trusted $3^{rd}$ party, a non-PII token to the PCT corresponding to the patient.

3. The computer-implemented method of claim 2, wherein the linking comprises:
generating a new non-PII token when the patient is determined to be a new patient; and
saving the new non-PII token in a repository.

4. The computer-implemented method of claim 2, wherein the linking comprises retrieving a previously-generated non-PII token when the patient is determined to be a repeat patient.

5. The computer-implemented method of claim 2, further comprising sending the non-PII token and the indication of the potential adverse reaction to the one or more pharmacies.

6. The computer-implemented method of claim 1, wherein the identifier corresponding to the prescription drug comprises one or more of: an imprint code; a generic name, a brand name, a chemical name, or a recommended international non-proprietary name.

7. The computer-implemented method of claim 1, wherein the URD is configured to store non-anonymized PII fields corresponding to the patient seeking the prescription drug.

8. A computer-implemented method for detecting and preventing prescription drug fraud, the method comprising:
receiving, at a main tokenizer, and from a trusted $3^{rd}$ party in communication with one or more pharmacies, one or more corresponding data sets comprising:

a subset of a plurality of personally identifiable information (PII) fields corresponding to a patient seeking a prescription drug prescribed by a physician;
a drug identifier corresponding to the prescription drug; and
a physician identifier corresponding to the physician;
determining, with one or more computer processors, relationships among the subset of the plurality of PII fields, the drug identifier, and the physician identifier by:
creating a core join data structure with at least a portion of all available patient and physician information;
splitting the core join data structure into persisted parts, wherein the persisted parts are configured for updating a shared structure between versions in memory to reduce disk utilization; and
updating the shared structure between the versions in the memory;
resolving, by the main tokenizer in communication with a universal reference database (URD) and based on the updated shared structure, an identity of the patient based on the subset of the plurality of PII fields and a persistent universal identifier corresponding to the patient;
linking a unique patient-centric token (PCT) to the patient based on the resolving;
determining, based on the one or more data sets, one or more over-prescription conditions of the prescription drug associated with the resolved identity of the patient; and
outputting the PCT and an indication of the over-prescription condition.

9. The computer-implemented method of claim 8, further comprising linking, by the trusted 3$^{rd}$ party, a non-PII token to the PCT corresponding to the patient.

10. The computer-implemented method of claim 9, wherein the linking comprises:
generating a new non-PII token when the patient is determined to be a new patient; and
saving the new non-PII token in a repository.

11. The computer-implemented method of claim 8, wherein the linking comprises retrieving a previously-generated non-PII token when the patient is determined to be a repeat patient.

12. The computer-implemented method of claim 8, further comprising sending the non-PII token and the indication of the over-prescription condition to the one or more pharmacies.

13. The computer-implemented method of claim 8, wherein the identifier corresponding to the prescription drug comprises one or more of: an imprint code; a generic name, a brand name, a chemical name, or a recommended international non-proprietary name.

14. The computer-implemented method of claim 8, wherein the URD is configured to store non-anonymized PII fields corresponding to the patient seeking the prescription drug.

15. A computer-implemented method, comprising:
receiving, at a main tokenizer and from a first trading partner, a first data set comprising a first subset of a plurality of personally identifiable information (PII) fields corresponding to an individual;
receiving, at the main tokenizer and from a second trading partner, a second data set comprising a second subset of the plurality of PII fields corresponding to the individual;
utilizing a token subscription service of a trusted 3$^{rd}$ party to control exchange of information between two or more of the first trading partner, the second trading partner, and the main tokenizer;
determining, with one or more computer processors, relationships among the first subset and the second subset of the plurality of PII fields and the individual by:
creating a core join data structure with at least a portion of all available individual and trading partner data;
splitting the core join data structure into persisted parts, wherein the persisted parts are configured for updating a shared structure between versions in memory to reduce disk utilization; and
updating the shared structure between the versions in the memory;
resolving, by the main tokenizer in communication with a universal reference database (URD) and based on the updated shared structure, the individual based on the first subset of the plurality of PII fields, the second subset of the plurality of PII fields, and a universal identifier corresponding to the individual;
linking a unique patient-centric token (PCT) to the individual based on the resolving;
generating a non-PII token linked to the individual, wherein the non-PII token is linked to the universal identifier corresponding to the individual; and
outputting one or more of the PCT and the non-PII token.

16. The computer-implemented method of claim 15, further comprising facilitating an exchange of the first subset of the plurality of PII fields and the second subset of the plurality of PII fields between the first trading partner and the second trading partner based on the non-PII token.

17. The computer-implemented method of claim 16, wherein facilitating the exchange of the first subset of the plurality of PII fields and the second subset of the plurality of PII fields between the first trading partner and the second trading partner is further based on de-identified matched data.

18. The computer-implemented method of claim 15, wherein the first subset is the same as the second subset.

19. The computer-implemented method of claim 15, wherein the first subset differs from the second subset.

20. The computer-implemented method of claim 15, wherein the non-PII token is linked to the universal identifier without requiring an SSN of the individual.

21. The computer-implemented method of claim 15, wherein one or more variations of PII in the first subset and the second subset is resolved to a same universal identifier.

22. The computer-implemented method of claim 15, wherein generating the non-PII token is based on one or more key identifying attributes comprising one or more of name, address, date of birth, and gender.

23. The computer-implemented method of claim 15, wherein the universal identifier is longitudinally consistent and based on comprehensive knowledge of a population of people.

24. The computer-implemented method of claim 15, further comprising:
receiving, at the main tokenizer and from the first trading partner, the non-PII token and the first subset of the plurality of PII fields corresponding to the individual;
receiving, at the main tokenizer and from the second trading partner, the non-PII token and the second subset of the plurality of PII fields corresponding to the individual;

generating, at the main tokenizer, and using the universal identifier, aggregated de-identified data corresponding to the individual based on the first subset of the plurality of PII fields, the second subset of the plurality of PII fields, and the non-PII token; and sending, to the first trading partner and the second trading partner, the non-PII token and the aggregated de-identified matched data corresponding to the individual.

25. The computer-implemented method of claim 15, further comprising:

generating de-identified matched data corresponding to the individual; and sending, to the first trading partner and the second trading partner, the non-PII token and the de-identified matched data corresponding to the first individual.

26. The computer-implemented method of claim 15, wherein the URD is configured to store non-anonymized PII fields corresponding to the individual.

* * * * *